(12) United States Patent
Okarski et al.

(10) Patent No.: US 12,616,519 B2
(45) Date of Patent: May 5, 2026

(54) BASKET ASSEMBLY WITH ATRAUMATIC TIP ELECTRODE AND METHODS OF MAKING THEREOF

(71) Applicant: Biosense Webster (Israel) Ltd., Yokneam (IL)

(72) Inventors: Kevin Mark Okarski, Monrovia, CA (US); Thanh Nguyen, El Monte, CA (US); Abubakarr Bah, Irvine, CA (US); Keshava Datta, Chino Hills, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 258 days.

(21) Appl. No.: 18/503,933

(22) Filed: Nov. 7, 2023

(65) Prior Publication Data

US 2024/0197391 A1    Jun. 20, 2024

Related U.S. Application Data

(60) Provisional application No. 63/387,593, filed on Dec. 15, 2022.

(51) Int. Cl.
     *A61B 18/14*          (2006.01)
     *A61B 17/00*          (2006.01)
     (Continued)

(52) U.S. Cl.
     CPC ..................... *A61B 18/1492* (2013.01); *A61B 2017/00185* (2013.01); *A61B 2017/00526* (2013.01);
     (Continued)

(58) Field of Classification Search
     CPC ...... A61B 18/1492; A61B 2017/00185; A61B 2017/00526; A61B 2018/00136;
     (Continued)

(56) References Cited

U.S. PATENT DOCUMENTS 4,699,147 A    10/1987   Chilson et al.
4,940,064 A     7/1990   Desai
     (Continued)

FOREIGN PATENT DOCUMENTS

CN     111248993 A     6/2020
CN     111248996 A     6/2020
     (Continued)

OTHER PUBLICATIONS

Extended European Search Report and Opinion dated May 16, 2024, from corresponding European Application No. 23216512.6.

*Primary Examiner* — Linda C Dvorak
*Assistant Examiner* — Abigail Bock

(57) ABSTRACT

The disclosed technology includes an expandable basket assembly for a medical probe, which may include a single unitary structure comprising a plurality of spines converging at a central spine intersection, the central spine intersection being positioned on a longitudinal axis of the expandable basket assembly at a distal end thereof. The plurality of spines may include a first layer and a second layer attached to the first layer and including a central cutout about the central spine intersection that exposes the first layer at the central spine intersection. The plurality of spine may include a central electrode attached to the first layer at the central spine intersection via a central aperture in the first layer at the central spine intersection. The second layer may be configured to articulate independently of the first layer at the central spine intersection.

20 Claims, 16 Drawing Sheets

(51) Int. Cl.
    *A61B 18/00*        (2006.01)
    *A61M 25/00*       (2006.01)

(52) U.S. Cl.
    CPC .............. *A61B 2018/00136* (2013.01); *A61B 2018/00148* (2013.01); *A61B 2018/0016* (2013.01); *A61B 2018/00267* (2013.01); *A61B 2018/00351* (2013.01); *A61B 2018/00577* (2013.01); *A61B 2018/00613* (2013.01); *A61B 2018/1475* (2013.01); *A61M 25/0015* (2013.01)

(58) Field of Classification Search
    CPC .. A61B 2018/00148; A61B 2018/0016; A61B 2018/00267; A61B 2018/00351; A61B 2018/00577; A61B 2018/00613; A61B 2018/1475; A61M 25/0015
    See application file for complete search history.

(56)               References Cited

U.S. PATENT DOCUMENTS

| | | | |
|---|---|---|---|
| 5,215,103 A | 6/1993 | Desai | |
| 5,255,679 A | 10/1993 | Imran | |
| 5,293,869 A | 3/1994 | Edwards et al. | |
| 5,309,910 A | 5/1994 | Edwards et al. | |
| 5,313,943 A | 5/1994 | Houser et al. | |
| 5,324,284 A | 6/1994 | Imran | |
| 5,345,936 A | 9/1994 | Pomeranz et al. | |
| 5,365,926 A | 11/1994 | Desai | |
| 5,396,887 A | 3/1995 | Imran | |
| 5,400,783 A | 3/1995 | Pomeranz et al. | |
| 5,411,025 A | 5/1995 | Webster, Jr. | |
| 5,415,166 A | 5/1995 | Imran | |
| 5,456,254 A | 10/1995 | Pietroski et al. | |
| 5,465,717 A | 11/1995 | Imran et al. | |
| 5,476,495 A | 12/1995 | Kordis et al. | |
| 5,499,981 A | 3/1996 | Kordis | |
| 5,526,810 A | 6/1996 | Wang | |
| 5,546,940 A | 8/1996 | Panescu et al. | |
| 5,549,108 A | 8/1996 | Edwards et al. | |
| 5,558,073 A | 9/1996 | Pomeranz et al. | |
| 5,577,509 A | 11/1996 | Panescu et al. | |
| 5,595,183 A | 1/1997 | Swanson et al. | |
| 5,598,848 A | 2/1997 | Swanson et al. | |
| 5,609,157 A | 3/1997 | Panescu et al. | |
| 5,628,313 A | 5/1997 | Webster, Jr. | |
| 5,681,280 A | 10/1997 | Rusk et al. | |
| 5,722,401 A | 3/1998 | Pietroski et al. | |
| 5,722,403 A | 3/1998 | McGee et al. | |
| 5,725,525 A * | 3/1998 | Kordis ................... A61B 5/287 606/41 |
| 5,730,128 A | 3/1998 | Pomeranz et al. | |
| 5,772,590 A | 6/1998 | Webster, Jr. | |
| 5,782,899 A | 7/1998 | Imran | |
| 5,823,189 A | 10/1998 | Kordis | |
| 5,881,727 A | 3/1999 | Edwards | |
| 5,893,847 A | 4/1999 | Kordis | |
| 5,904,680 A | 5/1999 | Kordis et al. | |
| 5,911,739 A | 6/1999 | Kordis et al. | |
| 5,928,228 A | 7/1999 | Kordis et al. | |
| 5,968,040 A | 10/1999 | Swanson et al. | |
| 6,014,579 A | 1/2000 | Pomeranz et al. | |
| 6,014,590 A | 1/2000 | Whayne et al. | |
| 6,119,030 A | 9/2000 | Morency | |
| 6,216,043 B1 | 4/2001 | Swanson et al. | |
| 6,216,044 B1 | 4/2001 | Kordis | |
| 6,428,537 B1 | 8/2002 | Swanson et al. | |
| 6,456,864 B1 | 9/2002 | Swanson et al. | |
| 6,574,492 B1 | 6/2003 | Ben-Haim et al. | |
| 6,584,345 B2 | 6/2003 | Govari | |
| 6,600,948 B2 | 7/2003 | Ben-Haim et al. | |
| 6,738,655 B1 | 5/2004 | Sen et al. | |
| 6,741,878 B2 | 5/2004 | Fuimaono et al. | |
| 6,748,255 B2 | 6/2004 | Fuimaono et al. | |

| | | | |
|---|---|---|---|
| 6,780,183 B2 | 8/2004 | Jimenez, Jr. et al. | |
| 6,837,886 B2 | 1/2005 | Collins et al. | |
| 6,866,662 B2 | 3/2005 | Fuimaono et al. | |
| 6,892,091 B1 | 5/2005 | Ben-Haim et al. | |
| 6,970,730 B2 | 11/2005 | Fuimaono et al. | |
| 6,973,340 B2 | 12/2005 | Fuimaono et al. | |
| 6,980,858 B2 | 12/2005 | Fuimaono et al. | |
| 7,048,734 B1 | 5/2006 | Fleischman et al. | |
| 7,149,563 B2 | 12/2006 | Fuimaono et al. | |
| 7,255,695 B2 | 8/2007 | Falwell et al. | |
| 7,257,434 B2 | 8/2007 | Fuimaono et al. | |
| 7,399,299 B2 | 7/2008 | Daniel et al. | |
| 7,410,486 B2 | 8/2008 | Fuimaono et al. | |
| 7,522,950 B2 | 4/2009 | Fuimaono et al. | |
| RE41,334 E | 5/2010 | Beatty et al. | |
| 7,846,157 B2 | 12/2010 | Kozel | |
| 7,930,018 B2 | 4/2011 | Harlev et al. | |
| 8,007,495 B2 | 8/2011 | McDaniel et al. | |
| 8,048,063 B2 | 11/2011 | Aeby et al. | |
| 8,103,327 B2 | 1/2012 | Harlev et al. | |
| 8,167,845 B2 | 5/2012 | Wang et al. | |
| 8,224,416 B2 | 7/2012 | De La Rama et al. | |
| 8,235,988 B2 | 8/2012 | Davis et al. | |
| 8,346,339 B2 | 1/2013 | Kordis et al. | |
| 8,435,232 B2 | 5/2013 | Aeby et al. | |
| 8,447,377 B2 | 5/2013 | Harlev et al. | |
| 8,498,686 B2 | 7/2013 | Grunewald | |
| 8,517,999 B2 | 8/2013 | Pappone et al. | |
| 8,545,490 B2 | 10/2013 | Mihajlovic et al. | |
| 8,560,086 B2 | 10/2013 | Just et al. | |
| 8,567,265 B2 | 10/2013 | Aeby et al. | |
| 8,712,550 B2 | 4/2014 | Grunewald | |
| 8,755,861 B2 | 6/2014 | Harlev et al. | |
| 8,825,130 B2 | 9/2014 | Just et al. | |
| 8,906,011 B2 | 12/2014 | Gelbart et al. | |
| 8,945,120 B2 | 2/2015 | McDaniel et al. | |
| 8,979,839 B2 | 3/2015 | De La Rama et al. | |
| 9,037,264 B2 | 5/2015 | Just et al. | |
| 9,131,980 B2 | 9/2015 | Bloom | |
| 9,204,929 B2 | 12/2015 | Solis | |
| 9,277,960 B2 | 3/2016 | Weinkam et al. | |
| 9,314,208 B1 | 4/2016 | Altmann et al. | |
| 9,339,331 B2 | 5/2016 | Tegg et al. | |
| 9,486,282 B2 | 11/2016 | Solis | |
| 9,554,718 B2 | 1/2017 | Bar-Tal et al. | |
| D782,686 S | 3/2017 | Werneth et al. | |
| 9,585,588 B2 | 3/2017 | Marecki et al. | |
| 9,597,036 B2 | 3/2017 | Aeby et al. | |
| 9,687,297 B2 | 6/2017 | Just et al. | |
| 9,693,733 B2 | 7/2017 | Altmann et al. | |
| 9,782,099 B2 | 10/2017 | Williams et al. | |
| 9,788,895 B2 | 10/2017 | Solis | |
| 9,801,681 B2 | 10/2017 | Laske et al. | |
| 9,814,618 B2 | 11/2017 | Nguyen et al. | |
| 9,833,161 B2 | 12/2017 | Govari | |
| 9,894,756 B2 | 2/2018 | Weinkam et al. | |
| 9,895,073 B2 | 2/2018 | Solis | |
| 9,907,609 B2 | 3/2018 | Cao et al. | |
| 9,974,460 B2 | 5/2018 | Wu et al. | |
| 9,986,949 B2 | 6/2018 | Govari et al. | |
| 9,993,160 B2 | 6/2018 | Salvestro et al. | |
| 10,014,607 B1 | 7/2018 | Govari et al. | |
| 10,028,376 B2 | 7/2018 | Weinkam et al. | |
| 10,034,637 B2 | 7/2018 | Harlev et al. | |
| 10,039,494 B2 | 8/2018 | Altmann et al. | |
| 10,045,707 B2 | 8/2018 | Govari | |
| 10,078,713 B2 | 9/2018 | Auerbach et al. | |
| 10,111,623 B2 * | 10/2018 | Jung ..................... A61B 5/287 |
| 10,130,420 B2 | 11/2018 | Basu et al. | |
| 10,136,828 B2 | 11/2018 | Houben et al. | |
| 10,143,394 B2 | 12/2018 | Solis | |
| 10,172,536 B2 | 1/2019 | Maskara et al. | |
| 10,182,762 B2 | 1/2019 | Just et al. | |
| 10,194,818 B2 | 2/2019 | Williams et al. | |
| 10,201,311 B2 | 2/2019 | Chou et al. | |
| 10,219,860 B2 | 3/2019 | Harlev et al. | |
| 10,219,861 B2 | 3/2019 | Just et al. | |
| 10,231,328 B2 | 3/2019 | Weinkam et al. | |
| 10,238,309 B2 | 3/2019 | Bar-Tal et al. | |

(56) References Cited

U.S. PATENT DOCUMENTS

| | | | |
|---|---|---|---|
| 10,278,590 | B2 | 5/2019 | Salvestro et al. |
| D851,774 | S | 6/2019 | Werneth et al. |
| 10,314,505 | B2 | 6/2019 | Williams et al. |
| 10,314,507 | B2 | 6/2019 | Govari et al. |
| 10,314,648 | B2 | 6/2019 | Ge et al. |
| 10,314,649 | B2 | 6/2019 | Bakos et al. |
| 10,349,855 | B2 | 7/2019 | Zeidan et al. |
| 10,350,003 | B2 | 7/2019 | Weinkam et al. |
| 10,362,991 | B2 | 7/2019 | Tran et al. |
| 10,375,827 | B2 | 8/2019 | Weinkam et al. |
| 10,376,170 | B2 | 8/2019 | Quinn et al. |
| 10,376,221 | B2 | 8/2019 | Iyun et al. |
| 10,398,348 | B2 | 9/2019 | Osadchy et al. |
| 10,403,053 | B2 | 9/2019 | Katz et al. |
| 10,441,188 | B2 | 10/2019 | Katz et al. |
| 10,470,682 | B2 | 11/2019 | Deno et al. |
| 10,470,714 | B2 | 11/2019 | Altmann et al. |
| 10,482,198 | B2 | 11/2019 | Auerbach et al. |
| 10,492,857 | B2 | 12/2019 | Guggenberger et al. |
| 10,542,620 | B2 | 1/2020 | Weinkam et al. |
| 10,575,743 | B2 | 3/2020 | Basu et al. |
| 10,575,745 | B2 | 3/2020 | Solis |
| 10,582,871 | B2 | 3/2020 | Williams et al. |
| 10,582,894 | B2 | 3/2020 | Ben Zrihem et al. |
| 10,596,346 | B2 | 3/2020 | Aeby et al. |
| 10,602,947 | B2 | 3/2020 | Govari et al. |
| 10,617,867 | B2 | 4/2020 | Viswanathan et al. |
| 10,660,702 | B2 | 5/2020 | Viswanathan et al. |
| 10,667,753 | B2 | 6/2020 | Werneth et al. |
| 10,674,929 | B2 | 6/2020 | Houben et al. |
| 10,681,805 | B2 | 6/2020 | Weinkam et al. |
| 10,682,181 | B2 | 6/2020 | Cohen et al. |
| 10,687,892 | B2 | 6/2020 | Long et al. |
| 10,702,178 | B2 | 7/2020 | Dahlen et al. |
| 10,716,477 | B2 | 7/2020 | Salvestro et al. |
| 10,758,304 | B2 | 9/2020 | Aujla |
| 10,765,371 | B2 | 9/2020 | Hayam et al. |
| 10,772,566 | B2 | 9/2020 | Aujila |
| 10,799,281 | B2 | 10/2020 | Goertzen et al. |
| 10,842,558 | B2 | 11/2020 | Harlev et al. |
| 10,842,561 | B2 | 11/2020 | Viswanathan et al. |
| 10,863,914 | B2 | 12/2020 | Govari et al. |
| 10,881,376 | B2 | 1/2021 | Shemesh et al. |
| 10,898,139 | B2 | 1/2021 | Guta et al. |
| 10,905,329 | B2 | 2/2021 | Bar-Tal et al. |
| 10,912,484 | B2 | 2/2021 | Ziv-Ari et al. |
| 10,918,306 | B2 | 2/2021 | Govari et al. |
| 10,939,871 | B2 | 3/2021 | Altmann et al. |
| 10,952,795 | B2 | 3/2021 | Cohen et al. |
| 10,973,426 | B2 | 4/2021 | Williams et al. |
| 10,973,461 | B2 | 4/2021 | Baram et al. |
| 10,987,045 | B2 | 4/2021 | Basu et al. |
| 11,006,902 | B1 | 5/2021 | Bonyak et al. |
| 11,040,208 | B1 | 6/2021 | Govari et al. |
| 11,045,628 | B2 | 6/2021 | Beeckler et al. |
| 11,051,877 | B2 | 7/2021 | Sliwa et al. |
| 11,109,788 | B2 | 9/2021 | Rottmann et al. |
| 11,116,435 | B2 | 9/2021 | Urman et al. |
| 11,129,574 | B2 | 9/2021 | Cohen et al. |
| 11,160,482 | B2 | 11/2021 | Solis |
| 11,164,371 | B2 | 11/2021 | Yellin et al. |
| 2004/0210121 | A1 | 10/2004 | Fuimaono et al. |
| 2006/0009689 | A1 | 1/2006 | Fuimaono et al. |
| 2006/0009690 | A1 | 1/2006 | Fuimaono et al. |
| 2006/0100669 | A1 | 5/2006 | Fuimaono et al. |
| 2007/0093806 | A1 | 4/2007 | Desai et al. |
| 2007/0276212 | A1 | 11/2007 | Fuimaono et al. |
| 2008/0234564 | A1 | 9/2008 | Beatty et al. |
| 2011/0118726 | A1 | 5/2011 | De La Rama et al. |
| 2011/0160574 | A1 | 6/2011 | Harlev et al. |
| 2011/0190625 | A1 | 8/2011 | Harlev et al. |
| 2011/0245756 | A1 | 10/2011 | Arora et al. |
| 2011/0301597 | A1 | 12/2011 | McDaniel et al. |
| 2013/0172872 | A1 | 7/2013 | Subramaniam et al. |
| 2013/0172883 | A1 | 7/2013 | Lopes et al. |
| 2013/0178850 | A1 | 7/2013 | Lopes et al. |
| 2013/0190587 | A1 | 7/2013 | Lopes et al. |
| 2013/0296852 | A1 | 11/2013 | Madjarov et al. |
| 2014/0025069 | A1 | 1/2014 | Willard et al. |
| 2014/0052118 | A1 | 2/2014 | Laske et al. |
| 2014/0180147 | A1 | 6/2014 | Thakur et al. |
| 2014/0180151 | A1 | 6/2014 | Maskara et al. |
| 2014/0180152 | A1 | 6/2014 | Maskara et al. |
| 2014/0257069 | A1 | 9/2014 | Eliason et al. |
| 2014/0276712 | A1 | 9/2014 | Mallin et al. |
| 2014/0309512 | A1 | 10/2014 | Govari et al. |
| 2015/0011991 | A1 | 1/2015 | Buysman et al. |
| 2015/0045863 | A1 | 2/2015 | Litscher et al. |
| 2015/0080693 | A1 | 3/2015 | Solis |
| 2015/0105770 | A1 | 4/2015 | Amit |
| 2015/0119878 | A1 | 4/2015 | Heisel et al. |
| 2015/0133919 | A1 | 5/2015 | McDaniel et al. |
| 2015/0208942 | A1 | 7/2015 | Bar-Tal et al. |
| 2015/0250424 | A1 | 9/2015 | Govari et al. |
| 2015/0270634 | A1 | 9/2015 | Buesseler et al. |
| 2015/0342532 | A1 | 12/2015 | Basu et al. |
| 2016/0081746 | A1 | 3/2016 | Solis |
| 2016/0113582 | A1 | 4/2016 | Altmann et al. |
| 2016/0113709 | A1 | 4/2016 | Maor |
| 2016/0183877 | A1 | 6/2016 | Williams et al. |
| 2016/0228023 | A1 | 8/2016 | Govari |
| 2016/0228062 | A1 | 8/2016 | Altmann et al. |
| 2016/0278853 | A1 | 9/2016 | Ogle et al. |
| 2016/0302858 | A1 | 10/2016 | Bencini |
| 2016/0338770 | A1* | 11/2016 | Bar-Tal ................... A61B 5/287 |
| 2017/0027638 | A1 | 2/2017 | Solis |
| 2017/0065227 | A1 | 3/2017 | Marrs et al. |
| 2017/0071543 | A1 | 3/2017 | Basu et al. |
| 2017/0071544 | A1 | 3/2017 | Basu et al. |
| 2017/0071665 | A1 | 3/2017 | Solis |
| 2017/0095173 | A1 | 4/2017 | Bar-Tal et al. |
| 2017/0100187 | A1 | 4/2017 | Basu et al. |
| 2017/0143227 | A1 | 5/2017 | Marecki et al. |
| 2017/0156790 | A1 | 6/2017 | Aujla |
| 2017/0172442 | A1 | 6/2017 | Govari |
| 2017/0185702 | A1 | 6/2017 | Auerbach et al. |
| 2017/0202515 | A1 | 7/2017 | Zrihem et al. |
| 2017/0221262 | A1 | 8/2017 | Laughner et al. |
| 2017/0224958 | A1 | 8/2017 | Cummings et al. |
| 2017/0265812 | A1 | 9/2017 | Williams et al. |
| 2017/0281031 | A1 | 10/2017 | Houben et al. |
| 2017/0281268 | A1 | 10/2017 | Tran et al. |
| 2017/0296125 | A1 | 10/2017 | Altmann et al. |
| 2017/0296251 | A1 | 10/2017 | Wu et al. |
| 2017/0347959 | A1 | 12/2017 | Guta et al. |
| 2017/0354338 | A1 | 12/2017 | Levin et al. |
| 2017/0354339 | A1 | 12/2017 | Zeidan et al. |
| 2017/0354364 | A1 | 12/2017 | Bar-Tal et al. |
| 2018/0008203 | A1 | 1/2018 | Iyun et al. |
| 2018/0028084 | A1 | 2/2018 | Williams et al. |
| 2018/0049803 | A1 | 2/2018 | Solis |
| 2018/0085064 | A1 | 3/2018 | Auerbach et al. |
| 2018/0132749 | A1 | 5/2018 | Govari et al. |
| 2018/0137687 | A1 | 5/2018 | Katz et al. |
| 2018/0160936 | A1 | 6/2018 | Govari et al. |
| 2018/0160978 | A1 | 6/2018 | Cohen et al. |
| 2018/0168511 | A1 | 6/2018 | Hall et al. |
| 2018/0184982 | A1 | 7/2018 | Basu et al. |
| 2018/0192958 | A1 | 7/2018 | Wu |
| 2018/0206792 | A1 | 7/2018 | Auerbach et al. |
| 2018/0235692 | A1 | 8/2018 | Efimov et al. |
| 2018/0249959 | A1 | 9/2018 | Osypka |
| 2018/0256109 | A1 | 9/2018 | Wu et al. |
| 2018/0279954 | A1 | 10/2018 | Hayam et al. |
| 2018/0303414 | A1 | 10/2018 | Toth et al. |
| 2018/0310987 | A1 | 11/2018 | Altmann et al. |
| 2018/0311497 | A1 | 11/2018 | Viswanathan et al. |
| 2018/0338722 | A1 | 11/2018 | Altmann et al. |
| 2018/0344188 | A1 | 12/2018 | Govari |
| 2018/0344202 | A1 | 12/2018 | Bar-Tal et al. |
| 2018/0344251 | A1 | 12/2018 | Harlev et al. |
| 2018/0344393 | A1 | 12/2018 | Gruba et al. |
| 2018/0360534 | A1 | 12/2018 | Teplitsky et al. |
| 2018/0365355 | A1 | 12/2018 | Auerbach et al. |

(56)        References Cited

U.S. PATENT DOCUMENTS

| | | |
|---|---|---|
| 2019/0000540 A1 | 1/2019 | Cohen et al. |
| 2019/0008582 A1 | 1/2019 | Govari et al. |
| 2019/0015007 A1 | 1/2019 | Rottmann et al. |
| 2019/0030328 A1 | 1/2019 | Stewart et al. |
| 2019/0053708 A1 | 2/2019 | Gliner |
| 2019/0059766 A1 | 2/2019 | Houben et al. |
| 2019/0069950 A1 | 3/2019 | Viswanathan et al. |
| 2019/0069954 A1 | 3/2019 | Cohen et al. |
| 2019/0117111 A1 | 4/2019 | Osadchy et al. |
| 2019/0117303 A1 | 4/2019 | Claude et al. |
| 2019/0117315 A1 | 4/2019 | Keyes et al. |
| 2019/0125439 A1 | 5/2019 | Rohl et al. |
| 2019/0133552 A1 | 5/2019 | Shemesh et al. |
| 2019/0142293 A1 | 5/2019 | Solis |
| 2019/0164633 A1 | 5/2019 | Ingel et al. |
| 2019/0167137 A1 | 6/2019 | Bar-Tal et al. |
| 2019/0167140 A1 | 6/2019 | Williams et al. |
| 2019/0188909 A1 | 6/2019 | Yellin et al. |
| 2019/0201664 A1 | 7/2019 | Govari |
| 2019/0209089 A1 | 7/2019 | Baram et al. |
| 2019/0216346 A1 | 7/2019 | Ghodrati et al. |
| 2019/0216347 A1 | 7/2019 | Ghodrati et al. |
| 2019/0231421 A1 | 8/2019 | Viswanathan et al. |
| 2019/0231423 A1 | 8/2019 | Weinkam et al. |
| 2019/0239811 A1 | 8/2019 | Just et al. |
| 2019/0246935 A1 | 8/2019 | Govari et al. |
| 2019/0298442 A1 | 10/2019 | Ogata et al. |
| 2019/0314083 A1 | 10/2019 | Herrera et al. |
| 2019/0328260 A1 | 10/2019 | Zeidan et al. |
| 2019/0343580 A1 | 11/2019 | Nguyen et al. |
| 2020/0000518 A1 | 1/2020 | Kiernan et al. |
| 2020/0008705 A1 | 1/2020 | Ziv-Ari et al. |
| 2020/0008869 A1 | 1/2020 | Byrd |
| 2020/0009378 A1 | 1/2020 | Stewart et al. |
| 2020/0015890 A1 | 1/2020 | To et al. |
| 2020/0022653 A1 | 1/2020 | Moisa |
| 2020/0029845 A1 | 1/2020 | Baram et al. |
| 2020/0046421 A1 | 2/2020 | Govari |
| 2020/0046423 A1 | 2/2020 | Viswanathan et al. |
| 2020/0060569 A1 | 2/2020 | Tegg |
| 2020/0077959 A1 | 3/2020 | Altmann et al. |
| 2020/0093539 A1 | 3/2020 | Long et al. |
| 2020/0129089 A1 | 4/2020 | Gliner et al. |
| 2020/0129125 A1 | 4/2020 | Govari et al. |
| 2020/0129128 A1 | 4/2020 | Gliner et al. |
| 2020/0179650 A1 | 6/2020 | Beeckler et al. |
| 2020/0196896 A1 | 6/2020 | Solis |
| 2020/0205689 A1 | 7/2020 | Squires et al. |
| 2020/0205690 A1 | 7/2020 | Williams et al. |
| 2020/0205737 A1 | 7/2020 | Beeckler |
| 2020/0205876 A1 | 7/2020 | Govari |
| 2020/0205892 A1 | 7/2020 | Viswanathan et al. |
| 2020/0206461 A1 | 7/2020 | Govari et al. |
| 2020/0206498 A1 | 7/2020 | Arora et al. |
| 2020/0289197 A1 | 9/2020 | Viswanathan et al. |
| 2020/0297234 A1 | 9/2020 | Houben et al. |
| 2020/0297281 A1 | 9/2020 | Basu et al. |
| 2020/0305726 A1 | 10/2020 | Salvestro et al. |
| 2020/0305946 A1 | 10/2020 | DeSimone et al. |
| 2020/0397328 A1 | 12/2020 | Altmann et al. |
| 2020/0398048 A1 | 12/2020 | Krimsky et al. |
| 2021/0015549 A1 | 1/2021 | Haghighi-Mood et al. |
| 2021/0022684 A1 | 1/2021 | Govari et al. |
| 2021/0045805 A1 | 2/2021 | Govari et al. |
| 2021/0059549 A1 | 3/2021 | Urman et al. |
| 2021/0059550 A1 | 3/2021 | Urman et al. |
| 2021/0059608 A1 | 3/2021 | Beeckler et al. |
| 2021/0059743 A1 | 3/2021 | Govari |
| 2021/0059747 A1 | 3/2021 | Krans et al. |
| 2021/0077180 A1 | 3/2021 | Govari et al. |
| 2021/0077184 A1 | 3/2021 | Basu et al. |
| 2021/0082157 A1 | 3/2021 | Rosenberg et al. |
| 2021/0085200 A1 | 3/2021 | Auerbach et al. |
| 2021/0085204 A1 | 3/2021 | Auerbach et al. |
| 2021/0085215 A1 | 3/2021 | Auerbach et al. |
| 2021/0085387 A1 | 3/2021 | Amit et al. |
| 2021/0093292 A1 | 4/2021 | Baram et al. |
| 2021/0093294 A1 | 4/2021 | Shemesh et al. |
| 2021/0093374 A1 | 4/2021 | Govari et al. |
| 2021/0093377 A1 | 4/2021 | Herrera et al. |
| 2021/0100612 A1 | 4/2021 | Baron et al. |
| 2021/0113822 A1 | 4/2021 | Beeckler et al. |
| 2021/0127999 A1 | 5/2021 | Govari et al. |
| 2021/0128010 A1 | 5/2021 | Govari et al. |
| 2021/0133516 A1 | 5/2021 | Govari et al. |
| 2021/0145282 A1 | 5/2021 | Bar-Tal et al. |
| 2021/0161592 A1 | 6/2021 | Altmann et al. |
| 2021/0162210 A1 | 6/2021 | Altmann et al. |
| 2021/0169421 A1 | 6/2021 | Govari |
| 2021/0169550 A1 | 6/2021 | Govari et al. |
| 2021/0169567 A1 | 6/2021 | Govari et al. |
| 2021/0169568 A1 | 6/2021 | Govari et al. |
| 2021/0177294 A1 | 6/2021 | Gliner et al. |
| 2021/0177356 A1 | 6/2021 | Gliner et al. |
| 2021/0177503 A1 | 6/2021 | Altmann et al. |
| 2021/0178166 A1 | 6/2021 | Govari et al. |
| 2021/0186363 A1 | 6/2021 | Gliner et al. |
| 2021/0186604 A1 | 6/2021 | Altmann et al. |
| 2021/0187241 A1 | 6/2021 | Govari et al. |
| 2021/0196372 A1 | 7/2021 | Altmann et al. |
| 2021/0196394 A1 | 7/2021 | Govari et al. |
| 2021/0212591 A1 | 7/2021 | Govari et al. |
| 2021/0219904 A1 | 7/2021 | Yarnitsky et al. |
| 2021/0278936 A1 | 9/2021 | Katz et al. |
| 2021/0282659 A1 | 9/2021 | Govari et al. |
| 2021/0307815 A1 * | 10/2021 | Govari .............. A61B 18/1206 |
| 2021/0308424 A1 | 10/2021 | Beeckler et al. |
| 2021/0338319 A1 | 11/2021 | Govari et al. |
| 2022/0054192 A1 | 2/2022 | Beeckler et al. |
| 2022/0079668 A1 | 3/2022 | Hall et al. |

FOREIGN PATENT DOCUMENTS

| | | | |
|---|---|---|---|
| EP | 0668740 A1 | 8/1995 | |
| EP | 0644738 B1 | 3/2000 | |
| EP | 0727183 B1 | 11/2002 | |
| EP | 0727184 B1 | 12/2002 | |
| EP | 2783651 A1 | 10/2014 | |
| EP | 2699151 B1 | 11/2015 | |
| EP | 2699152 B1 | 11/2015 | |
| EP | 2699153 B1 | 12/2015 | |
| EP | 2498706 B1 | 4/2016 | |
| EP | 2578173 B1 | 6/2017 | |
| EP | 3238645 A1 | 11/2017 | |
| EP | 2884931 B1 | 1/2018 | |
| EP | 2349440 B1 | 8/2019 | |
| EP | 3318211 B1 | 12/2019 | |
| EP | 3581135 A1 | 12/2019 | |
| EP | 2736434 B1 | 2/2020 | |
| EP | 3451962 B1 | 3/2020 | |
| EP | 3967253 A2 * | 3/2022 | ......... A61B 18/1492 |
| EP | 3972510 A1 | 3/2022 | |
| WO | 9421167 A1 | 9/1994 | |
| WO | 9421169 A1 | 9/1994 | |
| WO | 9625095 A1 | 8/1996 | |
| WO | 9634560 A1 | 11/1996 | |
| WO | 0182814 B1 | 5/2002 | |
| WO | 2004087249 A2 | 10/2004 | |
| WO | 2012100185 A2 | 7/2012 | |
| WO | 2013052852 A1 | 4/2013 | |
| WO | 2013162884 A1 | 10/2013 | |
| WO | 2013173917 A1 | 11/2013 | |
| WO | 2013176881 A1 | 11/2013 | |
| WO | 2014176205 A1 | 10/2014 | |
| WO | 2016019760 A1 | 2/2016 | |
| WO | 2016044687 A1 | 3/2016 | |
| WO | 2018111600 A1 | 6/2018 | |
| WO | 2018118798 A1 | 6/2018 | |
| WO | 2018191149 A1 | 10/2018 | |
| WO | 2019084442 A1 | 5/2019 | |
| WO | 2019143960 A1 | 7/2019 | |

(56)        References Cited

FOREIGN PATENT DOCUMENTS

| WO | 2020026217 | A1 | 2/2020 |
| WO | 2020206328 | A1 | 10/2020 |

* cited by examiner

120A

122A

123A

123B

123C

86

122B

BASKET ASSEMBLY WITH ATRAUMATIC TIP ELECTRODE AND METHODS OF MAKING THEREOF

CROSS-REFERENCE TO RELATED APPLICATION

This application claims, under 35 U.S.C. § 119(e), priority to and the benefit of U.S. Provisional Patent Application No. 63/387,593, filed Dec. 15, 2022, the entire contents of which are incorporated herein by reference.

FIELD

The present invention relates generally to medical devices, and in particular catheters with basket assemblies and electrodes, and further relates to, but not exclusively, catheters suitable for use to induce irreversible electroporation (IRE) of cardiac tissues.

BACKGROUND

Cardiac arrhythmias, such as atrial fibrillation (AF), occur when regions of cardiac tissue abnormally conduct electric signals to adjacent tissue. This disrupts the normal cardiac cycle and causes asynchronous rhythm. Certain procedures exist for treating arrhythmia, including surgically disrupting the origin of the signals causing the arrhythmia and disrupting the conducting pathway for such signals. By selectively ablating cardiac tissue by application of energy via a catheter, it is sometimes possible to cease or modify the propagation of unwanted electrical signals from one portion of the heart to another.

Many current ablation approaches in the art tend to utilize radiofrequency (RF) electrical energy to heat tissue. RF ablation can have certain rare drawbacks due to operator's skill, such as heightened risk of thermal cell injury which can lead to tissue charring, burning, steam pop, phrenic nerve palsy, pulmonary vein stenosis, and esophageal fistula. Cryoablation is an alternative approach to RF ablation that generally reduces thermal risks associated with RF ablation but may present tissue damage due to the very low temperature nature of such devices. Maneuvering cryoablation devices and selectively applying cryoablation, however, is generally more challenging compared to RF ablation; therefore cryoablation is not viable in certain anatomical geometries which may be reached by electrical ablation devices.

Some ablation approaches use irreversible electroporation (IRE) to ablate cardiac tissue using nonthermal ablation methods. IRE delivers short pulses of high voltage to tissues and generates an unrecoverable permeabilization of cell membranes. Delivery of IRE energy to tissues using multi-electrode catheters was previously proposed in the patent literature. Examples of systems and devices configured for IRE ablation are disclosed in U.S. Patent Pub. No. 2021/0169550A1, 2021/0169567A1, 2021/0169568A1, 2021/0161592A1, 2021/0196372A1, 2021/0177503A1, 2021/0186604A1, 2021/0162210, and 2021/0077180, each of which are incorporated herein by reference and attached in the Appendix included with priority application No. 63/387,593.

Regions of cardiac tissue can be mapped by a catheter to identify the abnormal electrical signals. The same or different catheter can be used to perform ablation. Some example catheters include a number of spines with electrodes positioned thereon. The electrodes are generally attached to the spines and secured in place by soldering, welding, or using an adhesive. Furthermore, multiple linear spines are generally assembled together by attaching both ends of the linear spines to a tubular shaft (e.g., a pusher tube) to form a spherical basket. Due to the small size of the spines and the electrodes, however, adhering the electrodes to the spines and then forming a spherical basket from the multiple linear spines can be a difficult task, increasing the manufacturing time and cost and the chances that the electrode fails due to an improper bond or misalignment. What is needed, therefore, are devices and methods of forming an improved basket assembly that can help to reduce the time required for manufacturing the basket assembly and alternative catheter geometries in general.

SUMMARY

Various embodiments of an expandable basket assembly for a medical probe and related methods are described and illustrated. An expandable basket assembly for a medical probe may include a single unitary structure comprising a plurality of spines converging at a central spine intersection, the central spine intersection being positioned on a longitudinal axis of the expandable basket assembly at a distal end thereof. The plurality of spines may include a first layer and a second layer attached to the first layer and including a central cutout about the central spine intersection that exposes the first layer at the central spine intersection. The plurality of spines may include a central electrode attached to the first layer at the central spine intersection via a central aperture in the first layer at the central spine intersection. The second layer may be configured to articulate independently of the first layer at the central spine intersection.

The first layer may include polyether ether ketone (PEEK), liquid crystal polymer (LCP), or both.

The plurality of spines may include four to ten spines of the plurality of spines.

The plurality of spines may include six spines.

The plurality of spines may form an approximately spherical shape.

The plurality of spines may form an approximately oblate-spheroid shape.

One or more electrodes may be coupled to each of the spines, each electrode may define a lumen through the electrode so that a spine extends through the lumen of each of the one or more electrodes.

Each electrode may include a wire relief adjacent the lumen to allow for one or more wires to extend adjacent to the lumen.

The lumen may be disposed symmetrically about a longitudinal axis of the electrode.

The one or more electrodes may be configured to deliver electrical pulses for irreversible electroporation, the pulses having a peak voltage of at least 900 volts (V).

The central electrode may be electrically isolated from the one or more electrodes coupled to each of the spines.

The central electrode may be spaced apart from the second layer.

The central electrode may include a disc- or button-shape.

The second layer may include a plurality of radial cutouts extending from the central cutout along the second layer of each spine.

The first layer may be an inner layer and the second layer may be an outer layer.

The first layer may be an outer layer and the first layer may be an outer layer.

In an aspect, an expandable basket assembly for a medical probe may include a single unitary structure comprising a plurality of spines converging at a central spine intersection, the central spine intersection being positioned on a longitudinal axis of the expandable basket assembly at a distal end thereof. The plurality of spines may include an outer layer, an inner layer attached to the outer layer, and one or more extrusion layers at least partially covering each spine. The expandable basket assembly also includes a central electrode attached to the outer layer at the central spine intersection via a central aperture in the outer layer at the central spine intersection and one or more electrodes attached to each spine and disposed over a portion of the one or more extrusion layers.

In an aspect, a method of constructing a medical probe includes cutting a planar sheet of a second material to form a second layer of a plurality of spines having a central spine intersection, cutting a center hole at the central spine intersection, overmolding a first material on the second layer for form a first layer, cutting aperture in the first layer at the central spine intersection, and inserting a central electrode into the aperture.

The method may further include attaching a first extrusion layer to partially cover end portions of each spine, attaching a second extrusion layer to cover each spine and the first extrusion layer covering each spine, inserting one or more ring electrodes around each spine, and fitting ends of the plurality of spines to a tubular shaft sized to traverse vasculature such that the central spine intersection is positioned at a distal end of the medical probe and respective spines are movable from a tubular configuration to a bowed configuration.

The method may further include cutting radial cutouts in the first material in each of the plurality of spines proximate the central spine intersection.

4

Figure 3A:
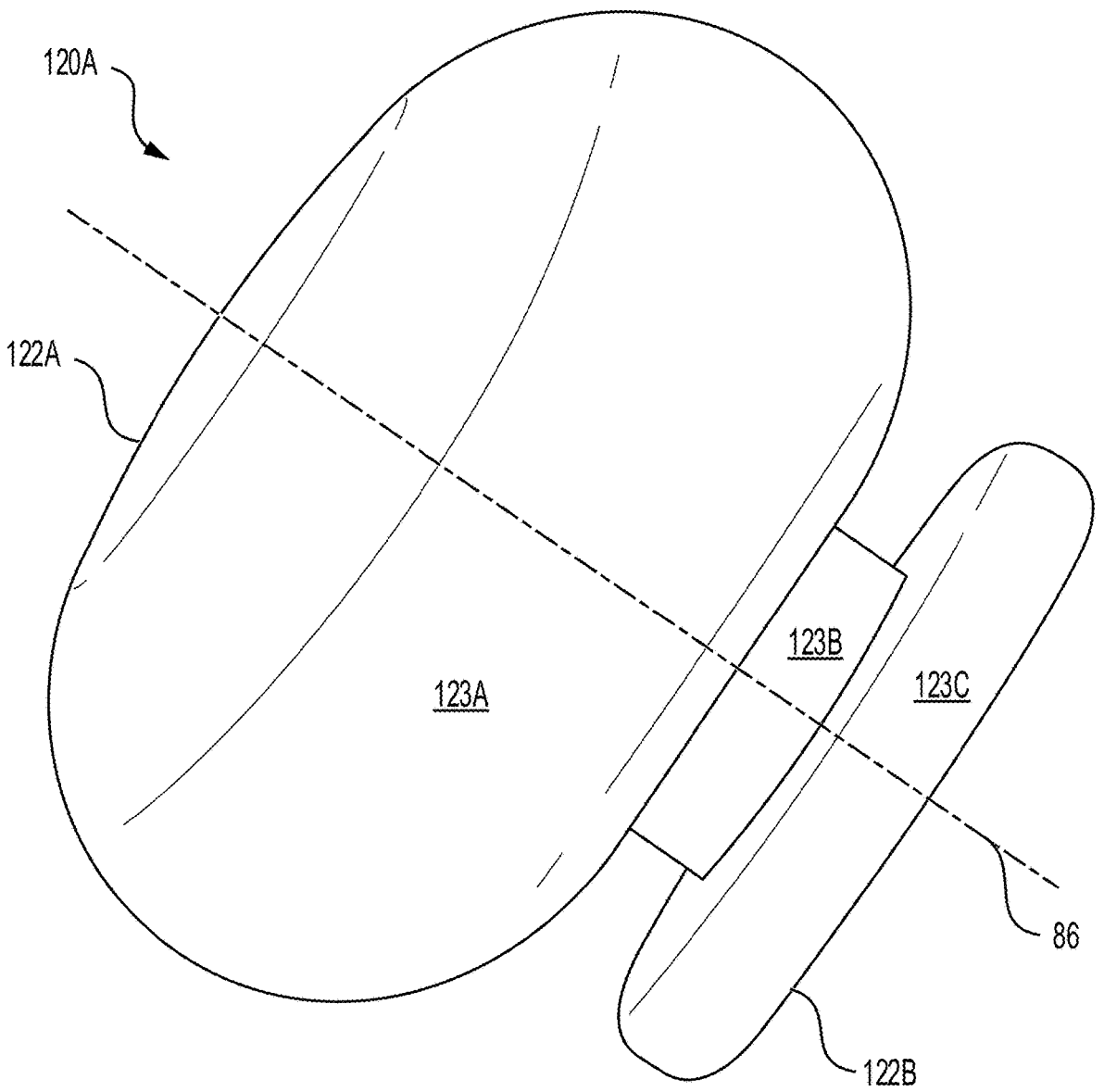
Figure 3B:
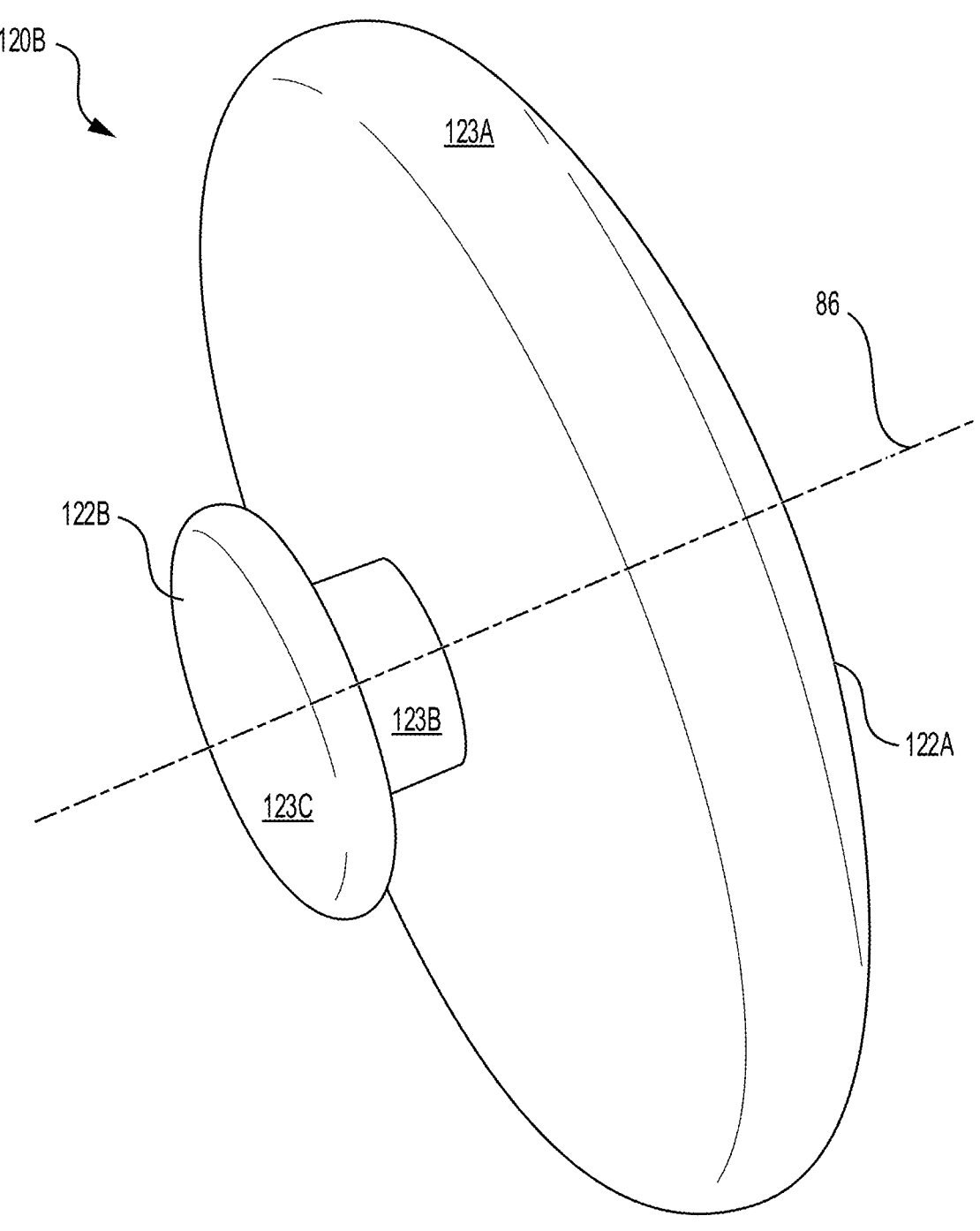
Figures 4A, 4B, 5:
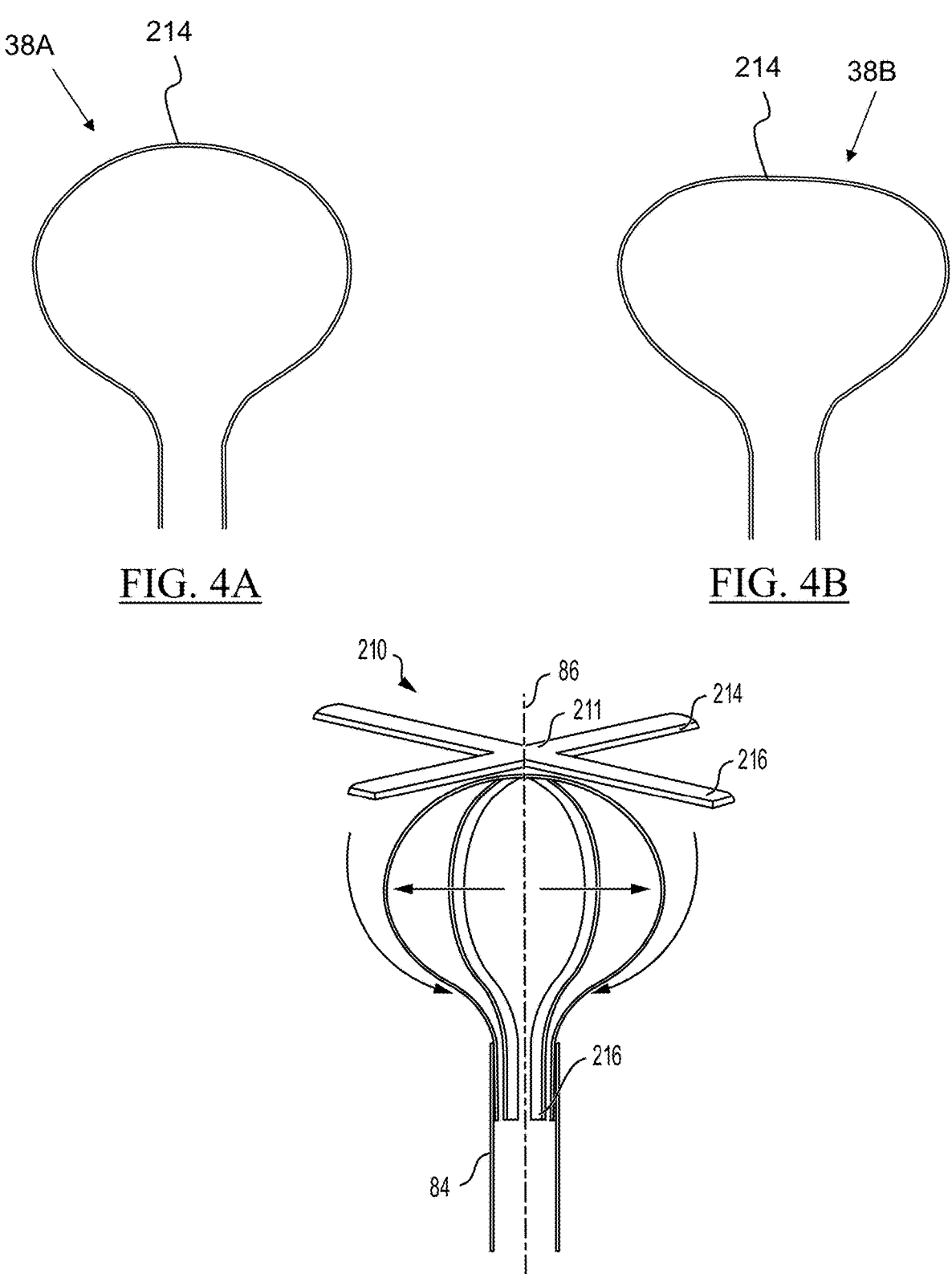
Figures 6A, 6B:
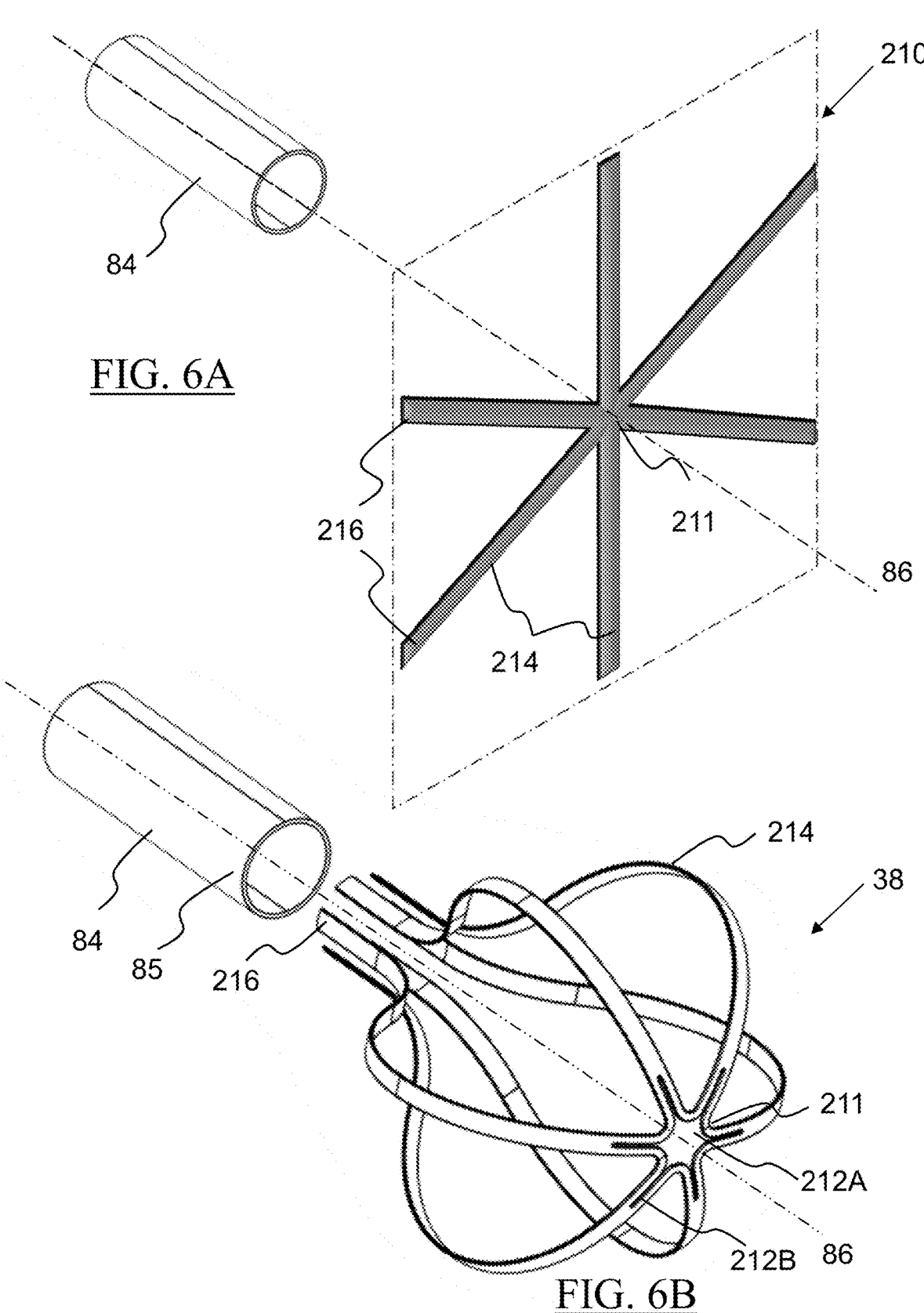
Figure 7:
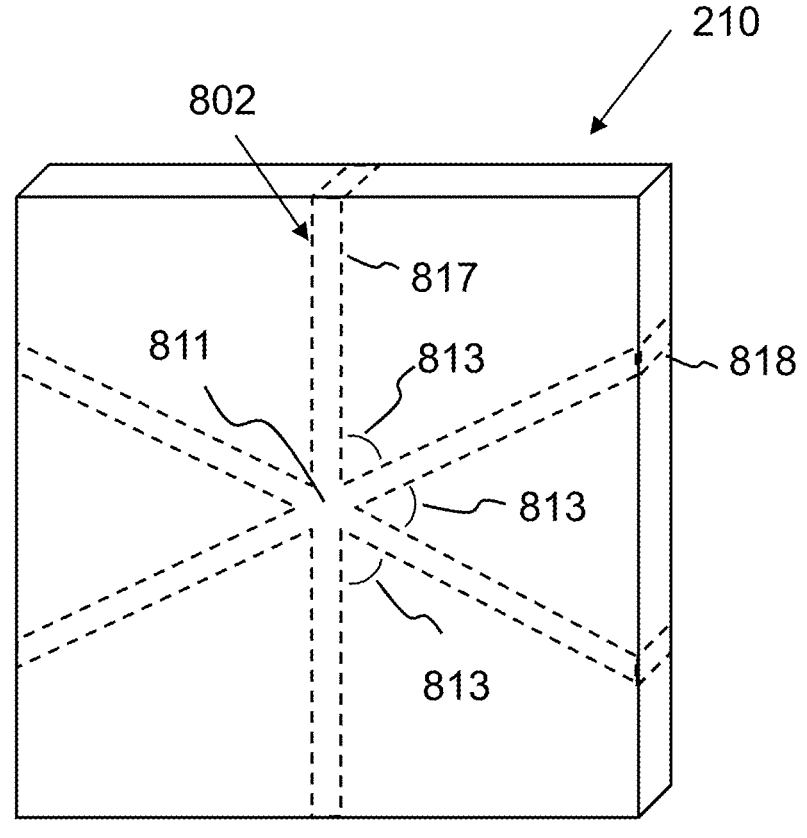
Figures 8A, 8B:
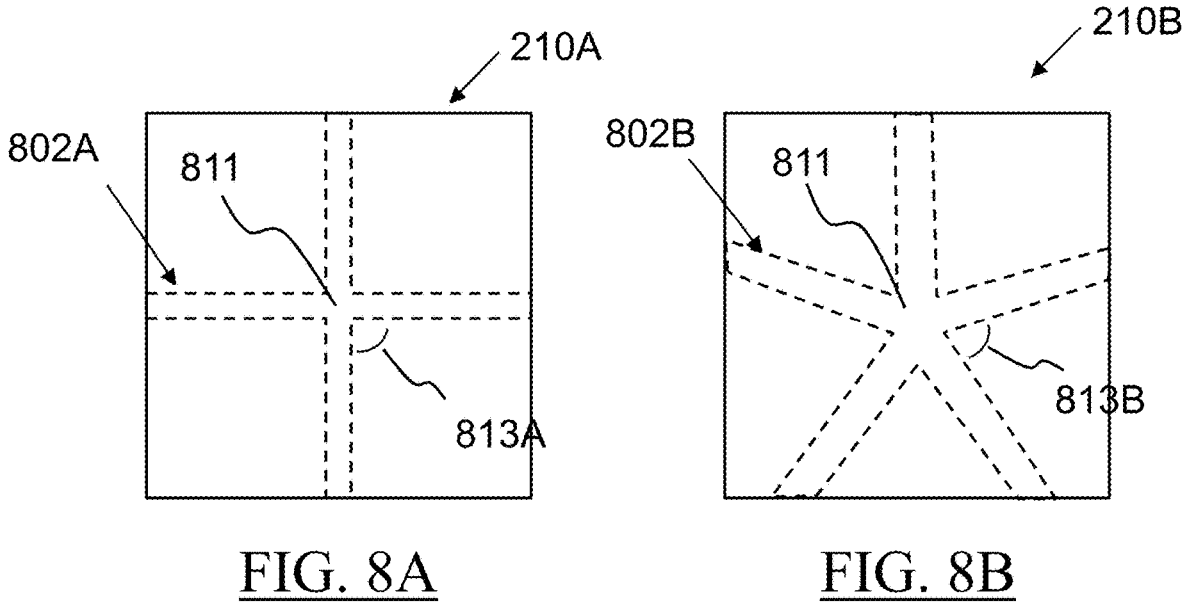
Figures 8C, 8D:
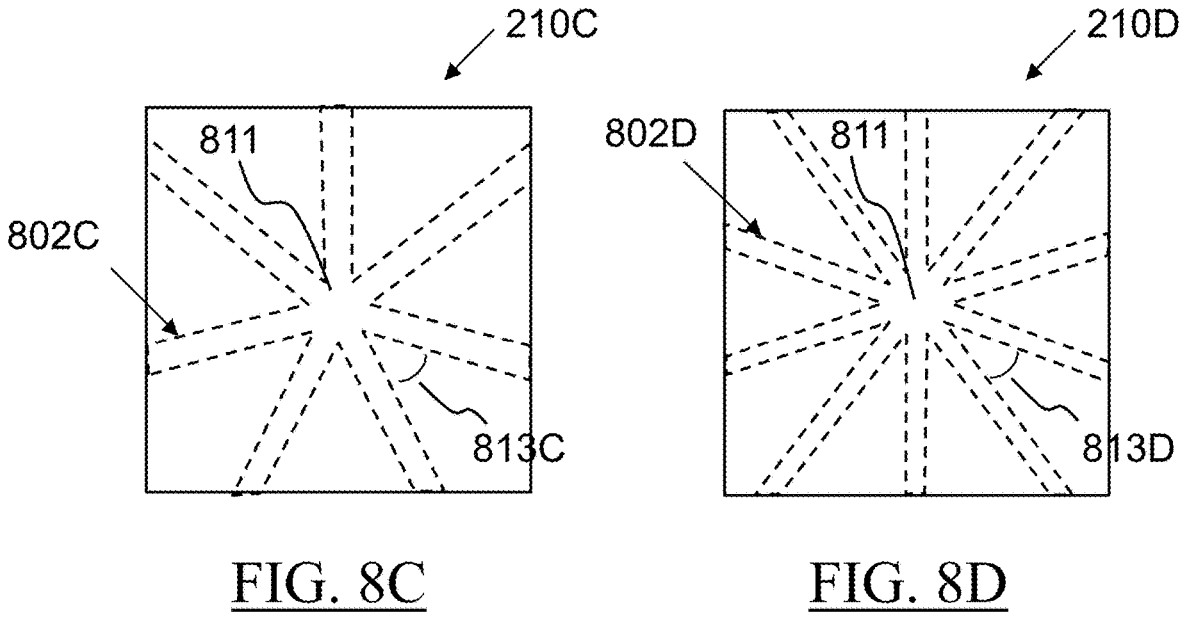
Figure 9:
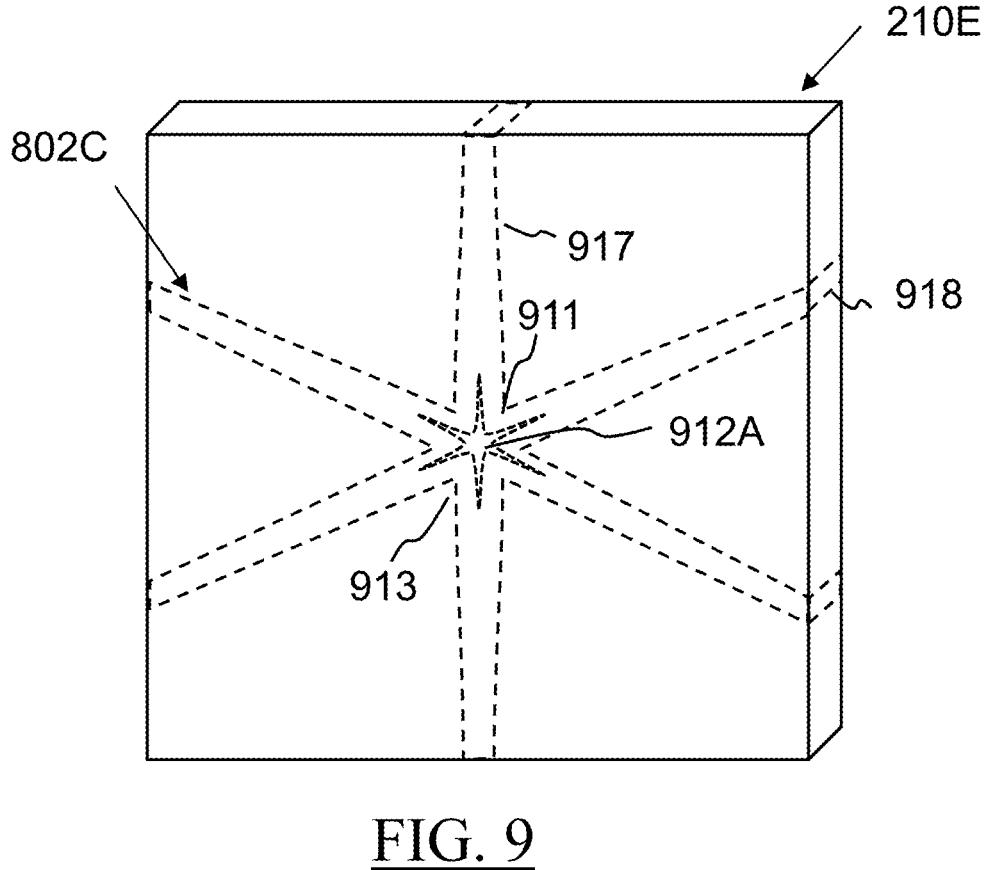
Figure 10:
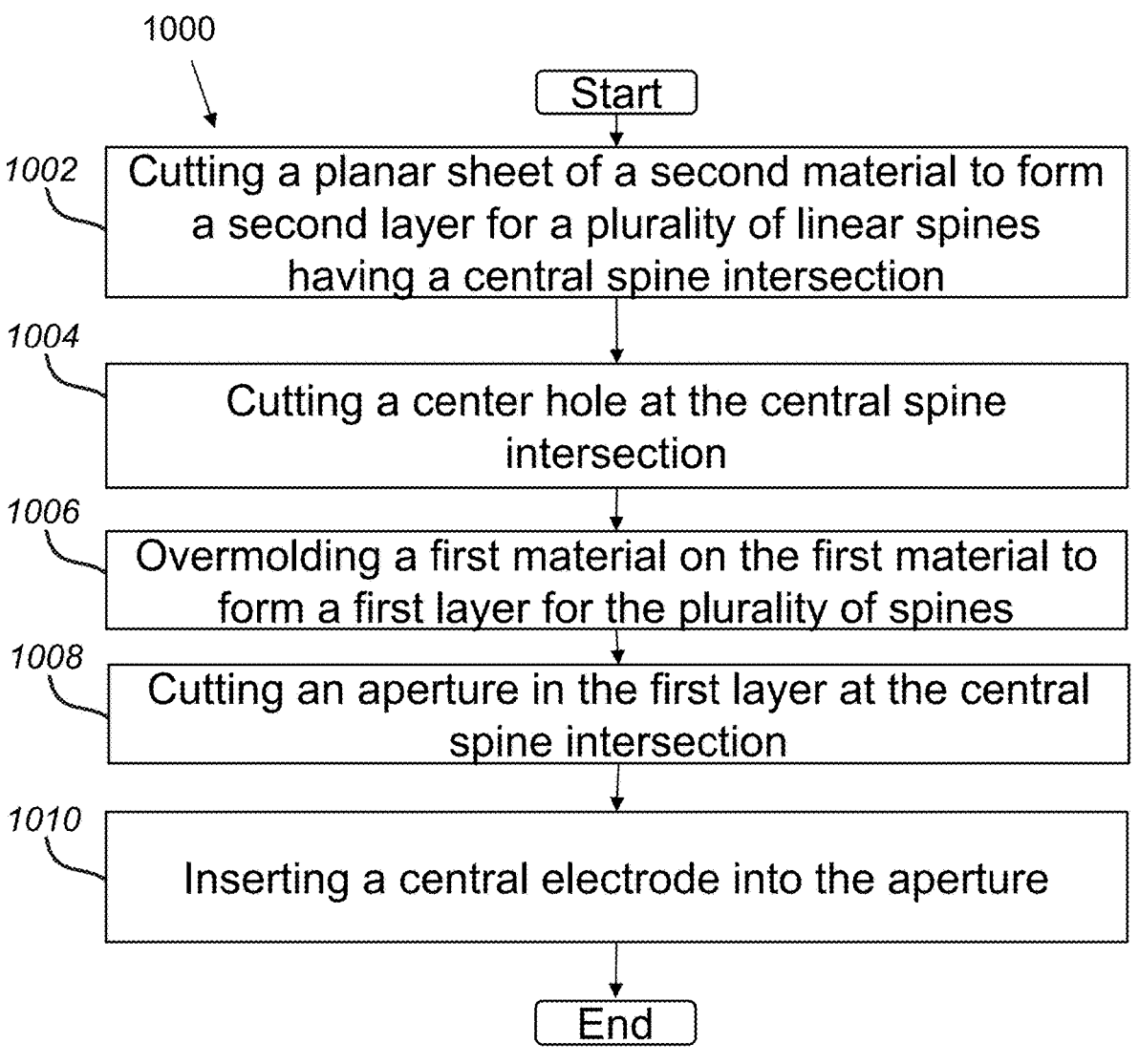

FIG. 3A is a schematic pictorial illustration showing a perspective view of a button shaped electrode for use with a medical probe, in accordance with an embodiment of the present invention;

FIG. 3B is a schematic pictorial illustration showing a perspective view of a disc shaped electrode for use with a medical probe, in accordance with an embodiment of the present invention;

FIGS. 4A and 4B are schematic pictorial illustrations showing a profile outline of a basket assembly of a given medical device, in accordance with embodiments of the present invention;

FIG. 5 is a schematic pictorial illustration showing a side view of a plurality of linear spines forming a basket assembly, in accordance with an embodiment of the present invention;

FIGS. 6A and 6B are schematic pictorial illustrations showing various insulative jackets of a given medical device, in accordance with embodiments of the present invention;

FIG. 7 is a schematic pictorial illustration of a method of cutting a plurality of linear spines from a planar sheet of material, in accordance with an embodiment of the present invention;

FIGS. 8A, 8B, 8C, and 8D are schematic pictorial illustrations of a method of cutting a plurality of linear spines from a planar sheet of material, in accordance with an embodiment of the present invention;

FIG. 9 is a schematic pictorial illustration of a method of cutting a plurality of linear spines including one or more cutouts at a central spine intersection from a planar sheet of material, in accordance with an embodiment of the present invention; and FIG. 10 is a flowchart illustrating a method of assembling a basket assembly, in accordance with an embodiment of the present invention.

DETAILED DESCRIPTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 71% to 110%.

As used herein, the terms "patient." "host." "user," and "subject" refer to any human or animal subject and are not intended to limit the systems or methods to human use, although use of the subject invention in a human patient represents a preferred embodiment. In addition, vasculature of a "patient," "host." "user," and "subject" can be vasculature of a human or any animal. It should be appreciated that an animal can be a variety of any applicable type, including, but not limited thereto, mammal, veterinarian animal, livestock animal or pet type animal, etc. As an example, the animal can be a laboratory animal specifically selected to have certain characteristics similar to a human (e.g., rat, dog, pig, monkey, or the like). It should be appreciated that the subject can be any applicable human patient, for example. As well, the term "proximal" indicates a location closer to the operator or physician whereas "distal" indicates a location further away to the operator or physician.

As discussed herein, "operator" can include a doctor, surgeon, technician, scientist, or any other individual or delivery instrumentation associated with delivery of a multi-electrode catheter for the treatment of drug refractory atrial fibrillation to a subject.

As discussed herein, the term "ablate" or "ablation", as it relates to the devices and corresponding systems of this disclosure, refers to components and structural features configured to reduce or prevent the generation of erratic cardiac signals in the cells by utilizing non-thermal energy, such as irreversible electroporation (IRE), referred throughout this disclosure interchangeably as pulsed electric field (PEF) and pulsed field ablation (PFA). Ablating or ablation as it relates to the devices and corresponding systems of this disclosure is used throughout this disclosure in reference to non-thermal ablation of cardiac tissue for certain conditions including, but not limited to, arrhythmias, atrial flutter ablation, pulmonary vein isolation, supraventricular tachycardia ablation, and ventricular tachycardia ablation. The term "ablate" or "ablation" also includes known methods, devices, and systems to achieve various forms of bodily tissue ablation as understood by a person skilled in the relevant art.

As discussed herein, the terms "bipolar" and "unipolar" when used to refer to ablation schemes describe ablation schemes which differ with respect to electrical current path and electric field distribution. "Bipolar" refers to ablation scheme utilizing a current path between two electrodes that are both positioned at a treatment site; current density and electric flux density is typically approximately equal at each of the two electrodes. "Unipolar" refers to ablation scheme utilizing a current path between two electrodes where one electrode including a high current density and high electric flux density is positioned at a treatment site, and a second electrode including comparatively lower current density and lower electric flux density is positioned remotely from the treatment site.

As discussed herein, the terms "biphasic pulse" and "monophasic pulse" refer to respective electrical signals. "Biphasic pulse" refers to an electrical signal including a positive-voltage phase pulse (referred to herein as "positive phase") and a negative-voltage phase pulse (referred to herein as "negative phase"). "Monophasic pulse" refers to an electrical signal including only a positive or only a negative phase. Preferably, a system providing the biphasic pulse is configured to prevent application of a direct current voltage (DC) to a patient. For instance, the average voltage of the biphasic pulse can be zero volts with respect to ground or other common reference voltage. Additionally, or alternatively, the system can include a capacitor or other protective component. Where voltage amplitude of the biphasic and/or monophasic pulse is described herein, it is understood that the expressed voltage amplitude is an absolute value of the approximate peak amplitude of each of the positive-voltage phase and/or the negative-voltage phase. Each phase of the biphasic and monophasic pulse preferably has a square shape including an essentially constant voltage amplitude during a majority of the phase duration. Phases of the biphasic pulse are separated in time by an interphase delay. The interphase delay duration is preferably less than or approximately equal to the duration of a phase of the biphasic pulse. The interphase delay duration is more preferably about 25% of the duration of the phase of the biphasic pulse.

As discussed herein, the terms "tubular" and "tube" are to be construed broadly and are not limited to a structure that is a right cylinder or strictly circumferential in cross-section or of a uniform cross-section throughout its length. For example, the tubular structures are generally illustrated as a substantially right cylindrical structure. However, the tubular structures may have a tapered or curved outer surface without departing from the scope of the present disclosure.

The term "temperature rating", as used herein, is defined as the maximum continuous temperature that a component can withstand during its lifetime without causing thermal damage, such as melting or thermal degradation (e.g., charring and crumbling) of the component.

The present disclosure is related to systems, methods or uses and devices which utilize end effectors including electrodes affixed to spines. Example systems, methods, and devices of the present disclosure may be particularly suited for IRE ablation of cardiac tissue to treat cardiac arrhythmias. Ablative energies are typically provided to cardiac tissue by a tip portion of a catheter which can deliver ablative energy alongside the tissue to be ablated. Some example catheters include three-dimensional structures at the tip portion and are configured to administer ablative energy from various electrodes positioned on the three-dimensional structures. Ablative procedures incorporating such example catheters can be visualized using fluoroscopy.

Ablation of cardiac tissue using application of a thermal technique, such as radio frequency (RF) energy and cryoablation, to correct a malfunctioning heart is a well-known procedure. Typically, to successfully ablate using a thermal technique, cardiac electropotentials need to be measured at various locations of the myocardium. In addition, temperature measurements during ablation provide data enabling the efficacy of the ablation. Typically, for an ablation procedure using a thermal technique, the electropotentials and the temperatures are measured before, during, and after the actual ablation.

RF approaches can have risks that can lead to tissue charring, burning, steam pop, phrenic nerve palsy, pulmonary vein stenosis, and esophageal fistula. Cryoablation is an alternative approach to RF ablation that can reduce some thermal risks associated with RF ablation. However maneuvering cryoablation devices and selectively applying cryoablation is generally more challenging compared to RF ablation; therefore, cryoablation is not viable in certain anatomical geometries which may be reached by electrical ablation devices.

IRE as discussed in this disclosure is a non-thermal cell death technology that can be used for ablation of atrial arrhythmias. To ablate using IRE/PEF, biphasic voltage pulses are applied to disrupt cellular structures of myocardium. The biphasic pulses are non-sinusoidal and can be tuned to target cells based on electrophysiology of the cells. In contrast, to ablate using RF, a sinusoidal voltage waveform is applied to produce heat at the treatment area, indiscriminately heating all cells in the treatment area. IRE therefore has the capability to spare adjacent heat sensitive structures or tissues which would be of benefit in the reduction of possible complications known with ablation or isolation modalities. Additionally, or alternatively, mono-phasic pulses can be utilized.

Electroporation can be induced by applying a pulsed electric field across biological cells to cause reversable (temporary) or irreversible (permanent) creation of pores in the cell membrane. The cells have a transmembrane elec-trostatic potential that is increased above a resting potential upon application of the pulsed electric field. While the transmembrane electrostatic potential remains below a threshold potential, the electroporation is reversable, mean-ing the pores can close when the applied pulse electric field is removed, and the cells can self-repair and survive. If the transmembrane electrostatic potential increases beyond the threshold potential, the electroporation is irreversible, and the cells become permanently permeable. As a result, the cells die due to a loss of homeostasis and typically die by programmed cell death or apoptosis, which is believed to leave less scar tissue as compared to other ablation modali-ties. Generally, cells of differing types have differing thresh-old potential. For instance, heart cells have a threshold potential of approximately 500 V/cm, whereas for bone it is 3000 V/cm. These differences in threshold potential allow IRE to selectively target tissue based on threshold potential.

The solution of this disclosure includes systems and methods for applying electrical signals from catheter elec-trodes positioned in the vicinity of myocardial tissue, pref-erably by applying a pulsed electric field effective to induce electroporation in the myocardial tissue. The systems and methods can be effective to ablate targeted tissue by induc-ing irreversible electroporation. In some examples, the sys-tems and methods can be effective to induce reversible electroporation as part of a diagnostic procedure. Reversible electroporation occurs when the electricity applied with the electrodes is below the electric field threshold of the target tissue allowing cells to repair. Reversible electroporation does not kill the cells but allows a physician to see the effect of reversible electroporation on electrical activation signals in the vicinity of the target location. Example systems and methods for reversible electroporation is disclosed in U.S. Patent Publication 2021/0162210, the entirety of which is incorporated herein by reference and attached in the Appen-dix included with priority application No. 63/387,593.

The pulsed electric field, and its effectiveness to induce reversible and/or irreversible electroporation, can be affected by physical parameters of the system and biphasic pulse parameters of the electrical signal. Physical param-eters can include electrode contact area, electrode spacing, electrode geometry, etc. examples presented herein gener-ally include physical parameters adapted to effectively induce reversible and/or irreversible electroporation. Bipha-sic pulse parameters of the electrical signal can include voltage amplitude, pulse duration, pulse interphase delay, inter-pulse delay, total application time, delivered energy, etc. In some examples, parameters of the electrical signal can be adjusted to induce both reversible and irreversible electroporation given the same physical parameters. Examples of various systems and methods of ablation including IRE are presented in U.S. Patent Publications 2021/0169550A1, 2021/0169567A1, 2021/0169568A1, 2021/0161592A1, 2021/0196372A1, 2021/0177503A1, 2021/0186604A1, 2021/10162210, and 2021/0077180 the entireties of each of which are incorporated herein by reference and attached in the Appendix included with pri-ority application No. 63/387,593.

To deliver pulsed field ablation (PFA) in an IRE (irre-versible electroporation) procedure, electrodes should con-tact the tissue being ablated with a sufficiently large surface area. As described hereinbelow, the medical probe includes a tubular shaft including proximal and distal ends, and a basket assembly at the distal end of the tubular shaft. The basket assembly includes a single unitary structure that includes a plurality of spines converging at a central spine intersection, which is positioned on a longitudinal axis of the expandable basket assembly at a distal end thereof. The plurality of spines includes a first layer and a second layer attached to the first layer. The second layer includes a central cutout about the central spine intersection that exposes the first layer at the central spine intersection. The medical probe also includes a central spine electrode attached to the first layer at the central spine intersection via a central aperture in the first layer at the central spine intersection. The second layer is configured to articulate independently of the first layer at the central spine intersection. One or more electrodes may be coupled to each of the spines. It is noted that the central electrode may be electrically isolated from the one or more electrode and may be spaced apart from the second layer so that it does not short. In addition, the central electrode may be used as a return electrode during ablation.

Figure 1:
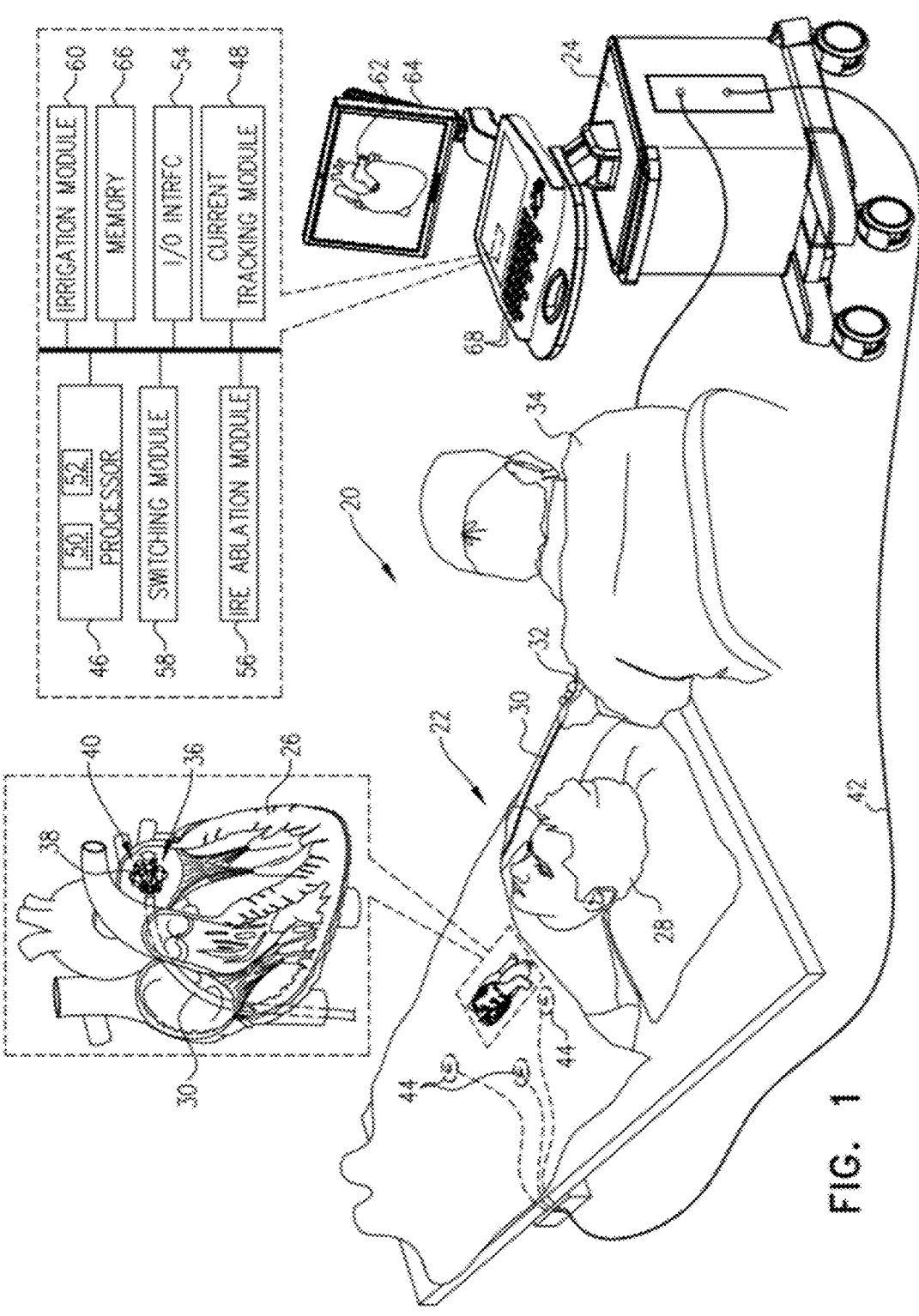
FIG. 1 is a schematic pictorial illustration of a medical system including a medical probe whose distal end includes a basket assembly with electrodes, in accordance with an embodiment of the present invention.

FIG. 1 is a schematic, pictorial illustration of a medical system 20 including a medical probe 22 and a control console 24, in accordance with an embodiment of the present invention. Medical system 20 may be based, for example, on the CARTO® system, produced by Biosense Webster Inc. of 31 Technology Drive, Suite 200, Irvine, CA 92618 USA. In embodiments described hereinbelow, medi-cal probe 22 can be used for diagnostic or therapeutic treatment, such as for performing ablation procedures in a heart 26 of a patient 28. Alternatively, medical probe 22 may be used, mutatis mutandis, for other therapeutic and/or diagnostic purposes in the heart or in other body organs.

Medical probe 22 includes a flexible insertion tube 30 and a handle 32 coupled to a proximal end of the tubular shaft. During a medical procedure, a medical professional 34 can insert probe 22 through the vascular system of patient 28 so that a distal end 36 of the medical probe enters a body cavity such as a chamber of heart 26. Upon distal end 36 entering the chamber of heart 26, medical professional 34 can deploy a basket assembly 38 approximate a distal end 36 of the medical probe 22. Basket assembly 38 can include a plu-rality of electrodes 40 affixed to a plurality of spines 214, as described in the description referencing FIGS. 2A-2G here-inbelow. To start performing a medical procedure such as irreversible electroporation (IRE) ablation, medical profes-sional 34 can manipulate handle 32 to position distal end 36 so that electrodes 40 engage cardiac tissue at a desired location or locations. Upon positioning the distal end 36 so that electrodes 40 engages cardiac tissue, the medical pro-fessional 34 can activate the medical probe 22 such that electrical pulses are delivered by the electrodes 40 to per-form the IRE ablation.

The medical probe 22 can include a guide sheath and a therapeutic catheter, wherein the guide sheath includes the flexible insertion tube 30 and the handle 32 and the thera-peutic catheter includes the basket assembly 38, electrodes 40, and a tubular shaft 84 (see FIGS. 2A-2G). The thera-peutic catheter is translated through the guide sheath so that the basket assembly 38 is positioned in the heart 26. The distal end 36 of the medical probe 22 corresponds to a distal end of the guide sheath when the basket assembly 38 is contained within the flexible insertion tube 30, and the distal end 36 of the medical probe 22 corresponds to a distal end of the basket assembly 38 when the basket assembly 38 is extended from the distal end of the guide sheath. The medical probe 22 can be alternatively configured to include a second handle on the therapeutic catheter and other features as understood by a person skilled in the pertinent art.

In the configuration shown in FIG. 1, control console 24 is connected, by a cable 42, to body surface electrodes, which typically include adhesive skin patches 44 that are affixed to patient 28. Control console 24 includes a processor 46 that, in conjunction with a tracking module 48, determines location coordinates of distal end 36 inside heart 26. Location coordinates can be determined based on electromagnetic position sensor output signals provided from the distal portion of the catheter when in the presence of a generated magnetic field. Location coordinates can additionally, or alternatively be based on impedances and/or currents measured between adhesive skin patches 44 and electrodes 40 that are affixed to basket assembly 38. In addition to being used as location sensors during a medical procedure, electrodes 40 may perform other tasks such as ablating tissue in the heart.

As described hereinabove, in conjunction with tracking module 48, processor 46 may determine location coordinates of distal end 36 inside heart 26 based on impedances and/or currents measured between adhesive skin patches 44 and electrodes 40. Such a determination is typically after a calibration process relating the impedances or currents to known locations of the distal end has been performed. While embodiments presented herein describe electrodes 40 that are preferably configured to deliver IRE ablation energy to tissue in heart 26, configuring electrodes 40 to deliver any other type of ablation energy to tissue in any body cavity is considered to be within the spirit and scope of the present invention. Furthermore, although described in the context of being electrodes 40 that are configured to deliver IRE ablation energy to tissue in the heart 26, one skilled in the art will appreciate that the disclosed technology can be applicable to electrodes used for mapping and/or determining various characteristics of an organ or other part of the patient's 28 body.

Processor 46 may include real-time noise reduction circuitry 50 typically configured as a field programmable gate array (FPGA), followed by an analog-to-digital (A/D) signal conversion integrated circuit 52. The processor can be programmed to perform one or more algorithms and uses circuitry 50 and circuit 52 as well as features of modules to enable the medical professional 34 to perform the IRE ablation procedure.

Control console 24 also includes an input/output (I/O) communications interface 54 that enables control console 24 to transfer signals from, and/or transfer signals to electrodes 40 and adhesive skin patches 44. In the configuration shown in FIG. 1, control console 24 additionally includes an IRE ablation module 56 and a switching module 58.

IRE ablation module 56 is configured to generate IRE pulses including peak power in the range of tens of kilowatts. In some examples, the electrodes 40 are configured to deliver electrical pulses including a peak voltage of at least 900 volts (V). The medical system 20 performs IRE ablation by delivering IRE pulses to electrodes 40. Preferably, the medical system 20 delivers biphasic pulses between electrodes 40 on the spine. Additionally, or alternatively, the medical system 20 delivers monophasic pulses between at least one of the electrodes 40 and a skin patch.

In order to dissipate the heat and to improve the efficiency of the ablation process, system 20 supplies irrigation fluid (e.g., a saline solution) to distal end 36 and to the electrodes 40 via a channel (not shown) in tubular shaft 84 (see FIGS.

2A through 2G). Additionally, or alternatively, irrigation fluid can be supplied through the flexible insertion tube 30. Control console 24 includes an irrigation module 60 to monitor and control irrigation parameters, such as the pressure and the temperature of the irrigation fluid. It is noted that while the preference for the exemplary embodiments of the medical probe is for IRE or PFA, it is within the scope of the present invention to also use the medical probe separately only for RF ablation (unipolar mode with an external grounding electrode or bipolar mode) or in combination with IRE and RF ablations sequentially (certain electrodes in IRE mode and other electrodes in RF mode) or simultaneously (groups of electrodes in IRE mode and other electrodes in RF mode).

Based on signals received from electrodes 40 and/or adhesive skin patches 44, processor 46 can generate an electroanatomical map 62 that shows the location of distal end 36 in the patient's body. During the procedure, processor 46 can present map 62 to medical professional 34 on a display 64, and store data representing the electroanatomical map in a memory 66. Memory 66 may include any suitable volatile and/or non-volatile memory, such as random-access memory or a hard disk drive.

In some embodiments, medical professional 34 can manipulate map 62 using one or more input devices 68. In alternative embodiments, display 64 may include a touchscreen that can be configured to accept inputs from medical professional 34, in addition to presenting map 62.

Figure 2A:
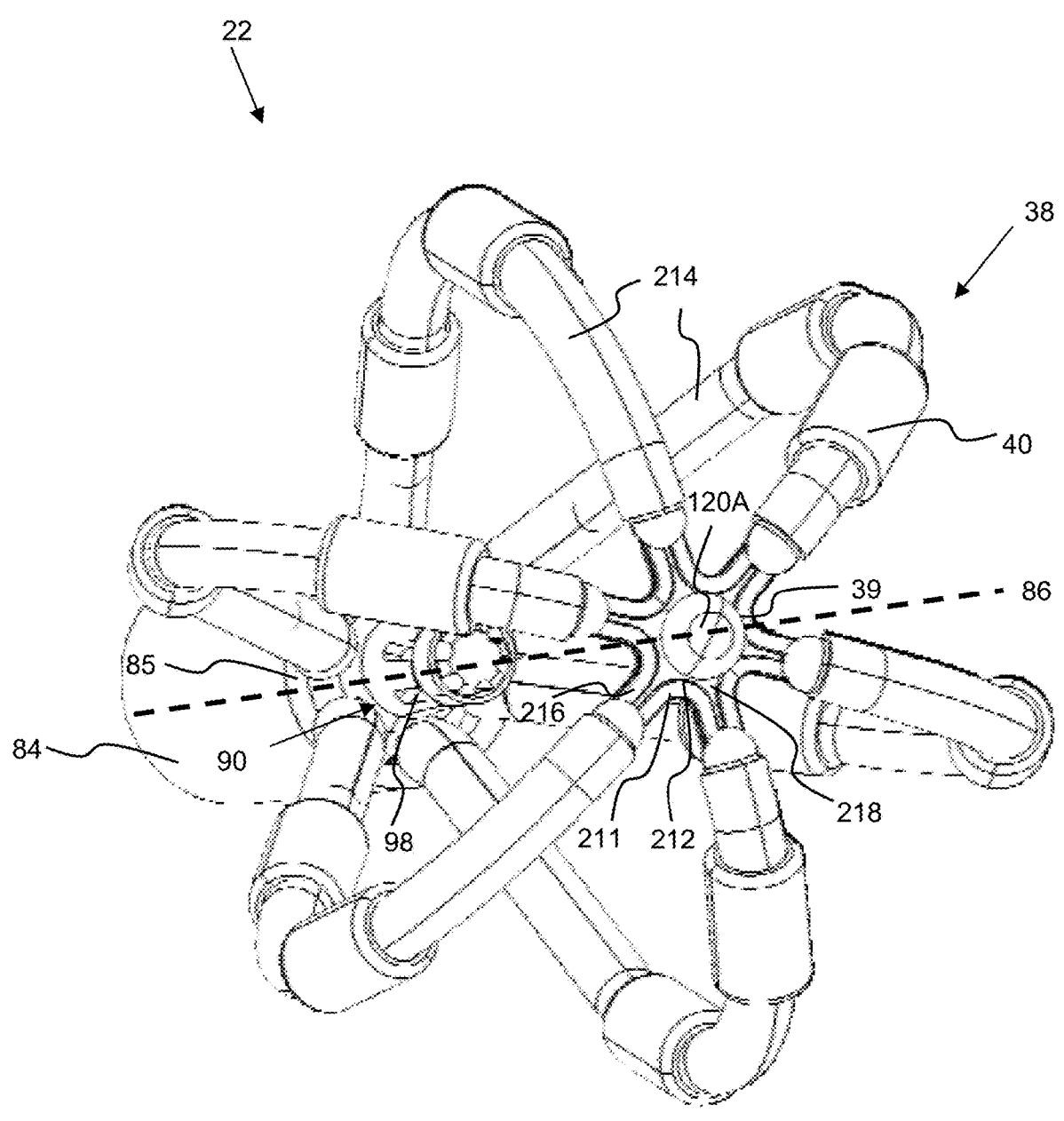
FIG. 2A is a schematic pictorial illustration showing a front perspective view of a medical probe in an expanded form, in accordance with an embodiment of the present invention.
Figure 2B:
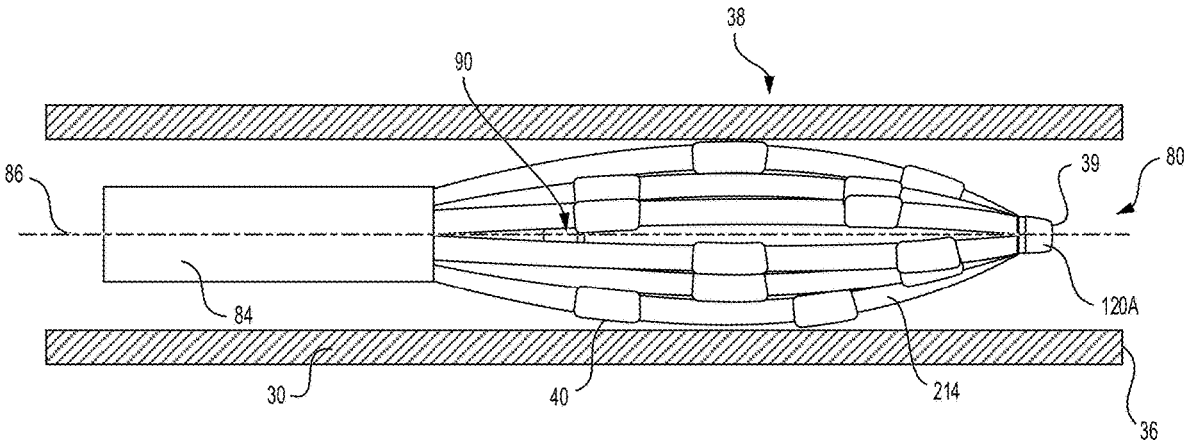
FIG. 2B is a schematic pictorial illustration showing a side perspective view of a medical probe in a semi-collapsed form, in accordance with embodiments of the present invention.

FIG. 2A is a schematic pictorial illustration showing a perspective view of a medical probe 22 including a basket assembly 38 in an expanded form when unconstrained, such as by being advanced out of an insertion tube lumen 80 (FIG. 2B) at a distal end 36 of an insertion tube 30 (FIG. 2B). The medical probe 22 illustrated in FIG. 2A lacks the guide sheath illustrated in FIG. 1. FIG. 2B shows the basket assembly in a collapsed form within insertion tube 30 of the guide sheath. In the expanded form (FIG. 2A), spines 214 bow radially outwardly and in the collapsed form (FIG. 2B) the spines are arranged generally along a longitudinal axis 86 of insertion tube 30.

As shown in FIG. 2A, basket assembly 38 includes a plurality of flexible spines 214 that are formed at the end of a tubular shaft 84 and are connected at both ends. During a medical procedure, medical professional 34 can deploy basket assembly 38 by extending tubular shaft 84 from insertion tube 30 causing basket assembly 38 to exit insertion tube 30 and transition to the expanded form. Spines 214 may have elliptical (e.g., circular) or rectangular (that may appear to be flat) cross-sections, and include a flexible, resilient material (e.g., a shape-memory alloy such as nickel-titanium, also known as Nitinol) forming a strut as will be described in greater detail herein.

As shown in FIG. 2A, the plurality of flexible linear spines 214 converge at a central spine intersection 211. In some exemplary central spine intersection 211 can include one or more cutouts 212 that allow for bending of the spines 214 when each spine respective attachment end 217 (FIG. 2C) is connected to the spine retention hub 90 which may include a flow diverter for irrigation fluid, described more below.

In embodiments described herein, one or more electrodes 40 positioned on spines 114 of basket assembly 38 can be configured to deliver ablation energy (RF and/or IRE) to tissue in heart 26. Additionally, or alternatively, the electrodes can also be used to determine the location of basket assembly 38 and/or to measure a physiological property such as local surface electrical potentials at respective locations on tissue in heart 26. The electrodes 40 can be biased such that a greater portion of the one or more electrodes 40 face outwardly from basket assembly 38 such that the one or more electrodes 40 deliver a greater amount of electrical energy outwardly away from the basket assembly 38 (i.e., toward the heart 26 tissue) than inwardly. Electrodes 40 are coupled to the spine 214 via bonding or fusion to hold the electrodes 40 in a fixed position on the spine 214.

Examples of materials ideally suited for forming electrodes 40 include gold, platinum and palladium (and their respective alloys). These materials also have high thermal conductivity which allows the minimal heat generated on the tissue (i.e., by the ablation energy delivered to the tissue) to be conducted through the electrodes to the back side of the electrodes (i.e., the portions of the electrodes on the inner sides of the spines), and then to the blood pool in heart 26.

Basket assembly 38 has a distal end 39. The medical probe 22 can include a spine retention hub 90 that extends longitudinally from a distal end of tubular shaft 84 towards distal end 39 of basket assembly 38. As described supra, control console 24 includes irrigation module 60 that delivers irrigation fluid to basket assembly 38 through tubular shaft 84.

Figure 2C:
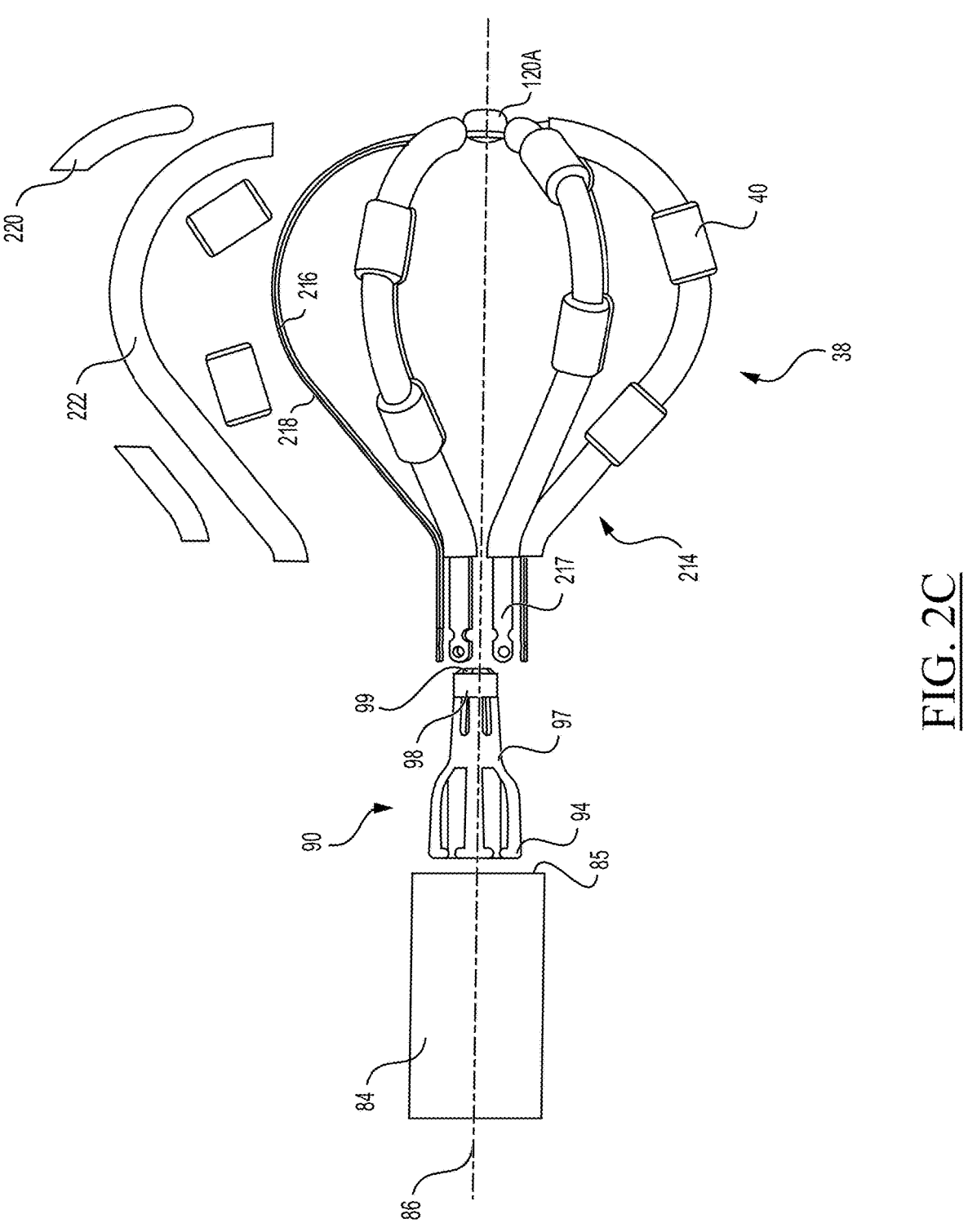
FIG. 2C is a schematic pictorial illustration showing an exploded side view of a medical probe, in accordance with an embodiment of the present invention.
Figure 2D:
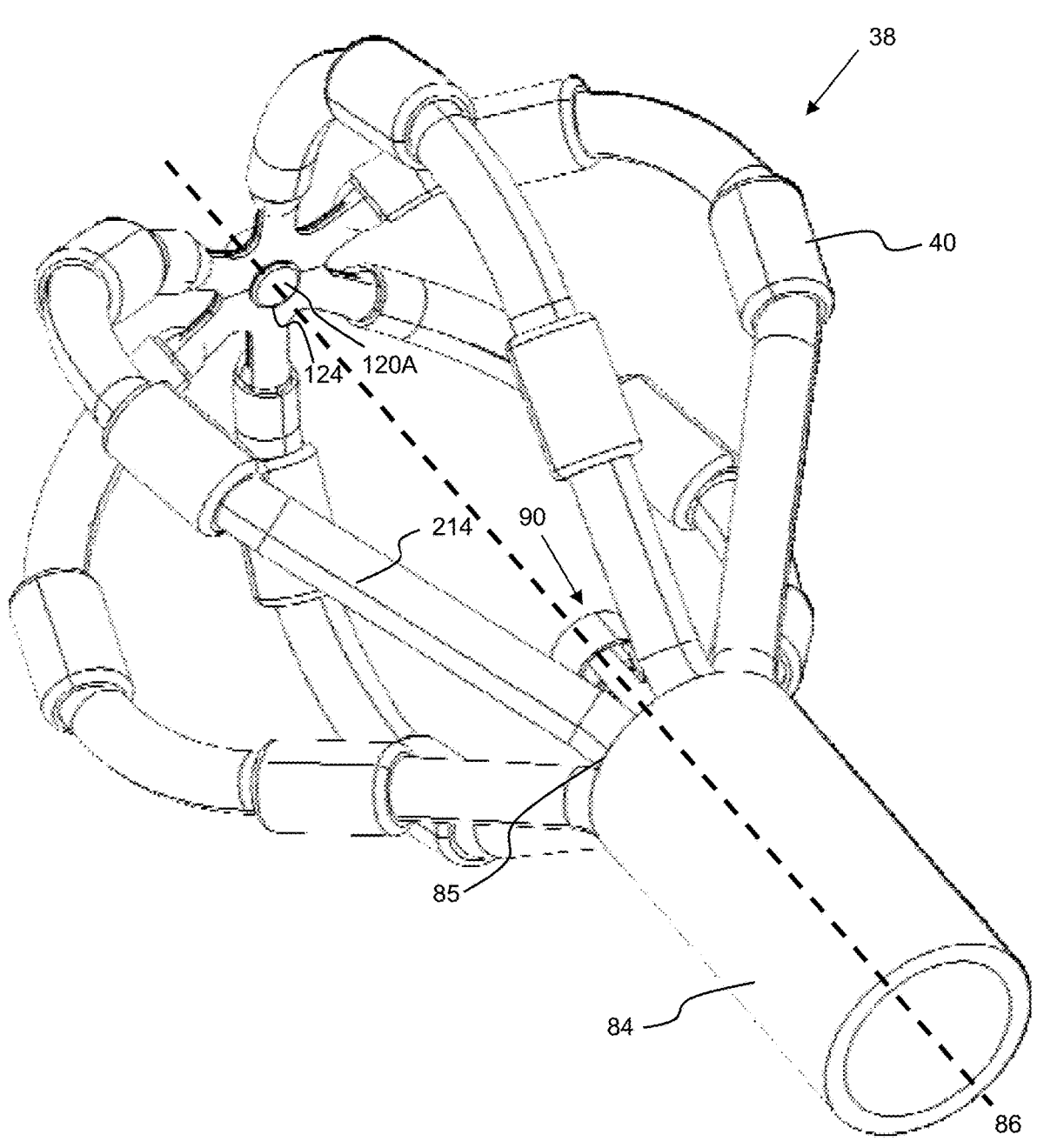
FIG. 2D is schematic pictorial illustration showing a back perspective view of a medical probe, in accordance with an embodiment of the present invention.
Figure 2E:
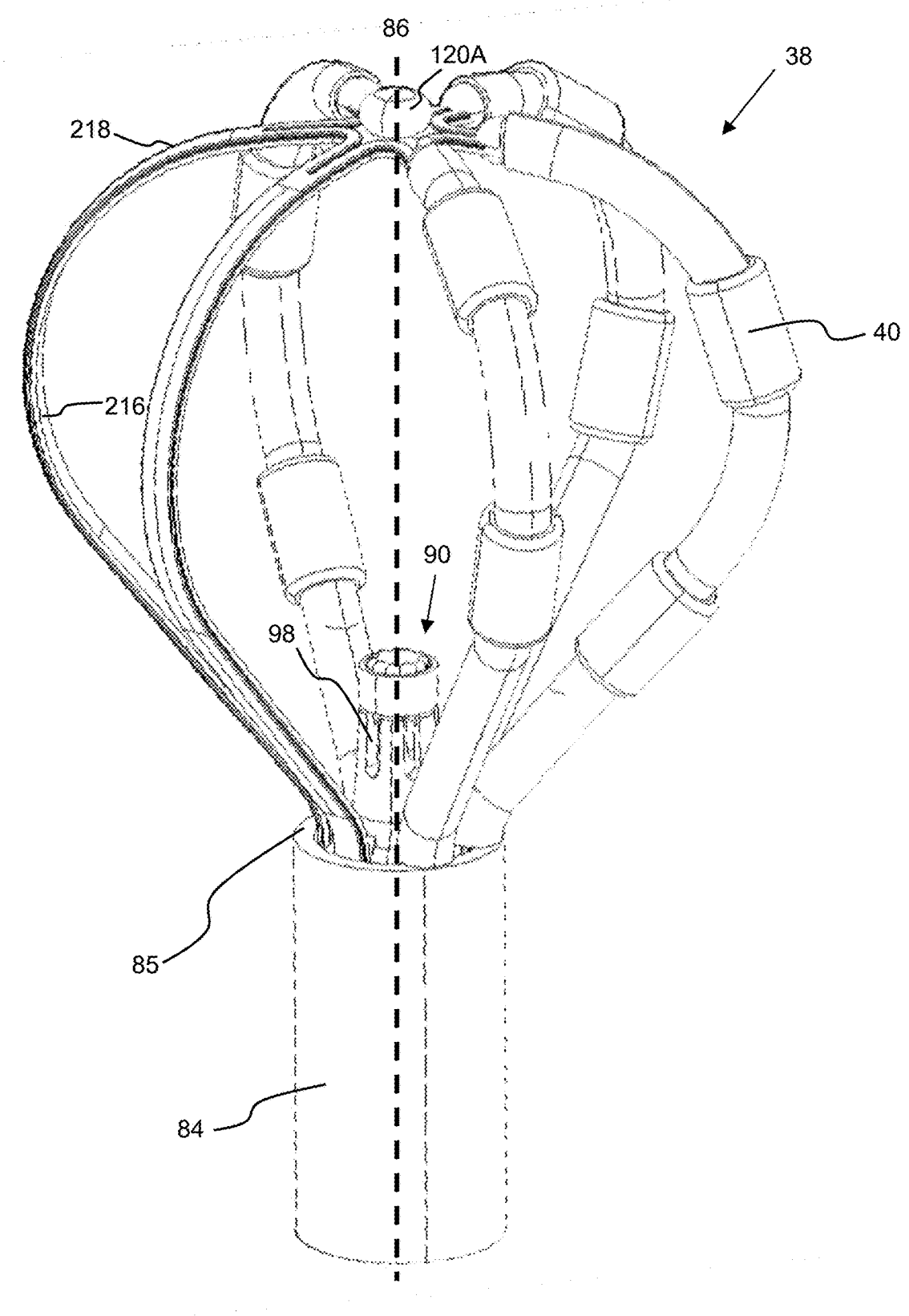
FIG. 2E is a schematic pictorial illustration showing a side perspective view of a medical probe in expanded form, in accordance with an embodiment of the present invention.
Figure 2F:
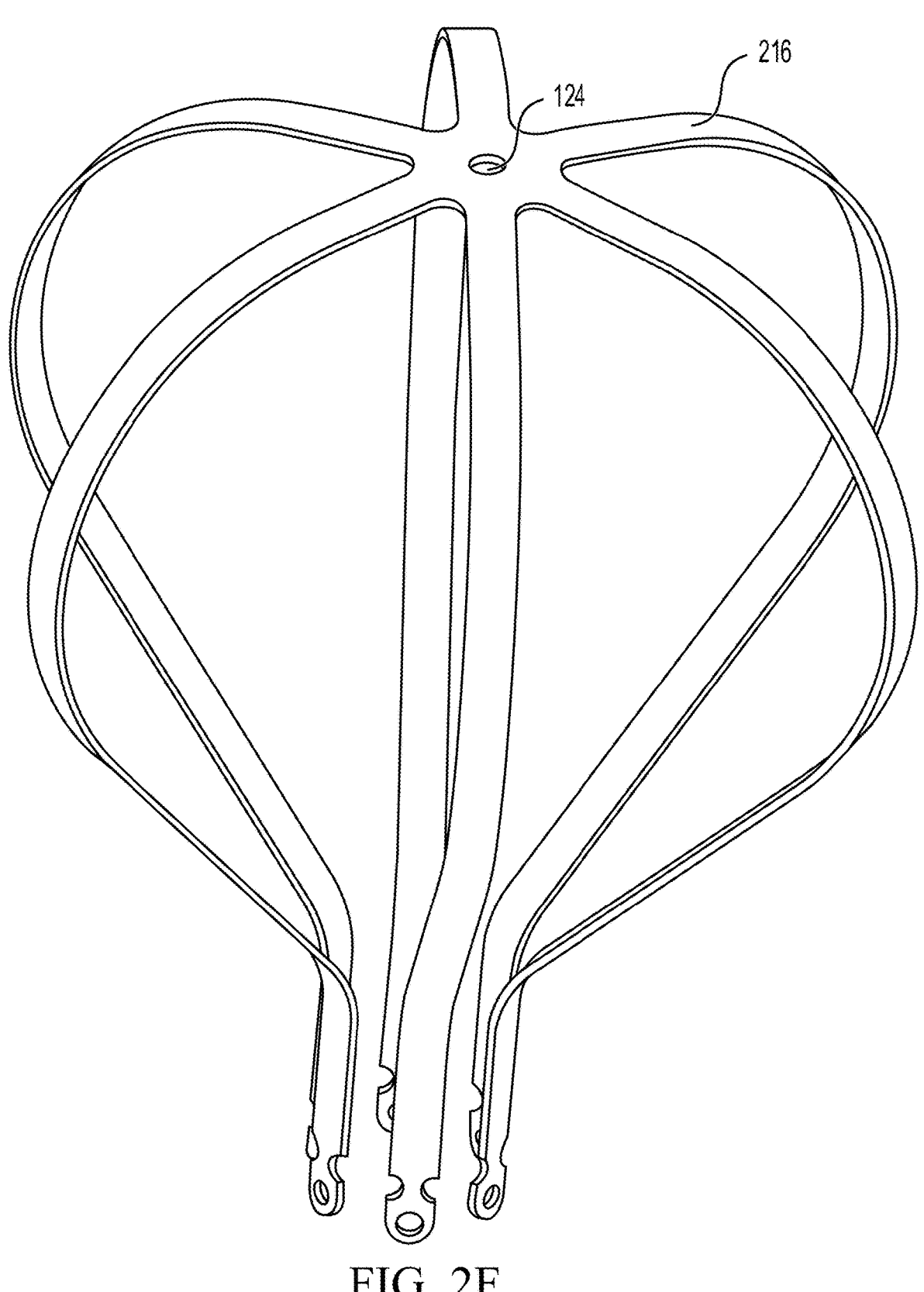
FIG. 2F is a schematic pictorial illustration showing a perspective view of a first layer of the expandable basket assembly, in accordance with an embodiment of the present invention.

As shown in FIGS. 2A-2E, the plurality of flexible spines 214 may include a first layer 216 and a second layer 218 attached to the first layer 216. The second layer 218 may include a central cutout about the central spine intersection that exposes the first layer at the central spine intersection. The first layer 216 may include polyether ether keytone (PEEK), liquid crystal polymer (LCP), or both. The second layer 218 may include nitinol, cobalt chromium, or both. As shown in FIGS. 2D and 2F, the first layer 216 may have an (e.g., circular) aperture 124 for connecting the central electrode 120A to the first layer 216. Additionally, as shown in FIG. 2A, the second layer 218 may include a central cutout 212 taking a shape and size (e.g., FIGS. 2A and 9) that exposes the first layer 216 about the central spine intersection 211 to enable the central electrode 120A to be able to connect with the first layer 216 without contacting the second layer 218.

Figure 2G:
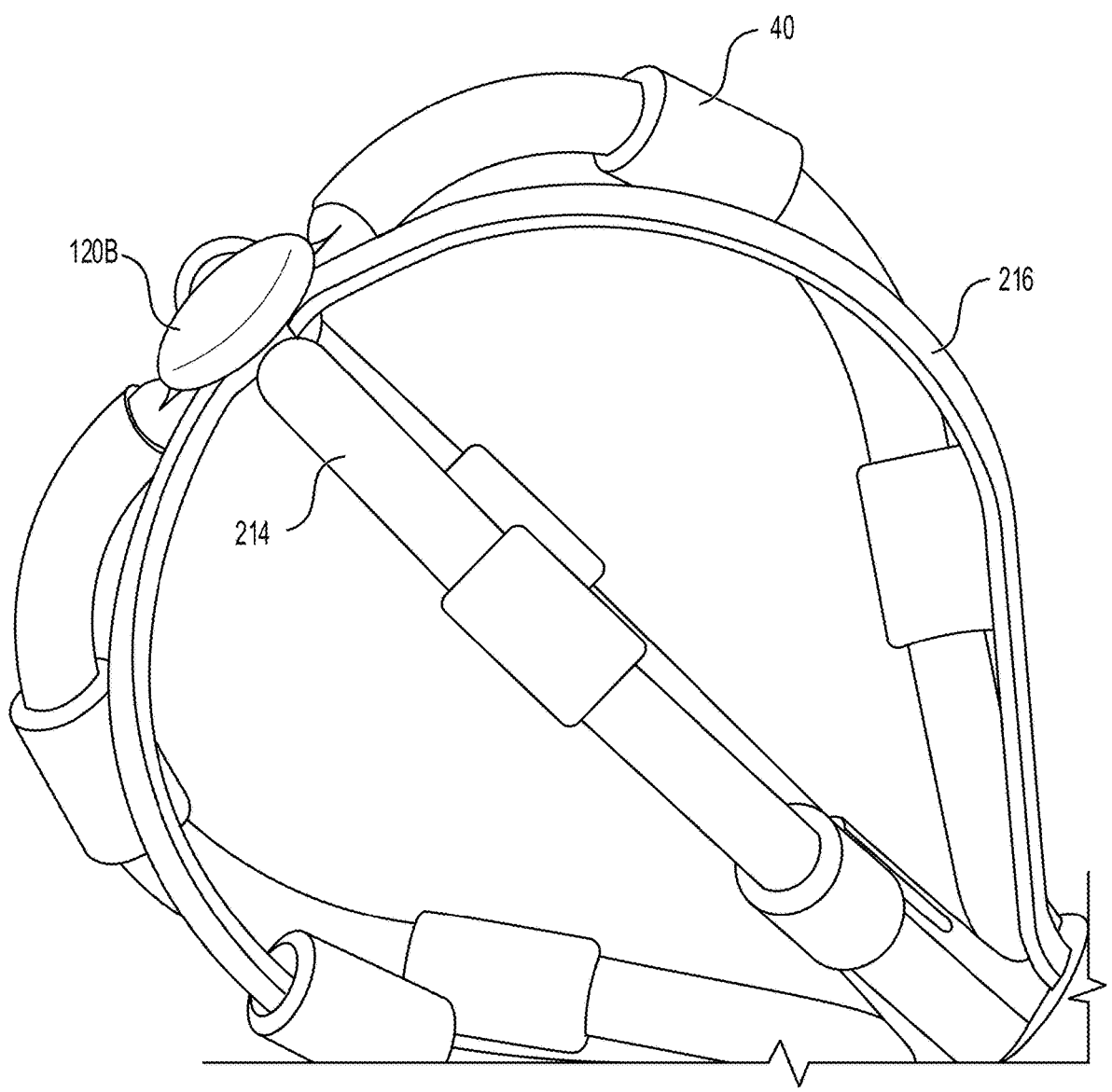
FIG. 2G is a schematic pictorial illustration showing a perspective view of a medical probe with a disc-shaped electrode, in accordance with an embodiment of the present invention.

Basket assembly 38 may include a central electrode 120A that is attached to the first layer 216 at the central spine intersection 211 via a central aperture 212 in the first layer at the central spine intersection 211. The central electrode 120A may be electrically isolated from the one or more electrodes 40 to prevent shorting between the electrodes. In addition, the central electrode 120A may be spaced apart from the second layer for the same reasons. Furthermore, the central electrode 120A may be used as return electrode in conjunction with the one or more electrodes 40 during ablation. As shown in FIGS. 2A-2E and 3A, central electrode 120A may have a button-shape having a distal end 122A and a proximal end 122B with a tissue contacting portion 123A proximate the distal end, a constrained portion 123B proximate the contacting portion 123A, and a back portion 122C proximate the constrained portion 123B. The constrained portion 123B may have a diameter that is less than diameters of the contacting portion 123A and the back portion 122C. Additionally, the back portion 122C may have a diameter that is less than the contacting portion 123A. As shown in FIGS. 2G and 3B, central electrode 120B may have a disc shape having a distal end 122A and proximal end 122B and may also include similar contacting portion 123A, constrained portions 123B, and back portion 122C.

Although FIGS. 2A-2G, 3A, and 3B show button and disc shapes, the central electrode 120A may be of any shape so long as it has a constrained portion 123B that is constrained in a direction that is perpendicular to a longitudinal direction 86 extending from the proximal end 122B to the distal end 122A.

Turning to FIG. 2C, basket assembly 38 includes a single unitary structure that includes a plurality of linear spines 214 formed from a planar sheet of material 210 (shown more clearly in FIGS. 5, 6A, and 7). The spines 214 may be concealed and covered by at least one or more extrusion layers 220, 222, which electrode 40 are disposed around. The one or more extrusion layer 220, 222 may include two halves connect to each other and enable be placed around each spine 214. In other embodiments, the one or more extrusion layers 220, 222 may be overmolded on each spine 214 or over end portions of each spine 214 as is the case for extrusion layers 220. The spine retention hub 90 can be inserted into the tubular shaft 84 and attached to the tubular shaft 84. Spine retention hub 90 can include a cylindrical member 94 including a plurality of relief lands 96, an upper portion 97, and multiple irrigation openings 98 positioned about the upper portion 97, and at least one spine retention hub electrode 99, or some combination thereof. Relief lands 96 can be disposed on the outer surface of cylindrical member 94 and configured to allow a portion of each spine 214, such as each spine attachment end 217, to be fitted into a respective relief land 96. The attachment end 217 can be a generally linear end of the spine 214. The attachment end 217 can be configured to extend outwardly from the spine retention hub 90 such that the basket assembly 38 is positioned outwardly from the spine retention hub 90 and, consequently, outwardly from the tubular shaft 84. In this way, the spine 214 can be configured to position the basket assembly 38 distally from the distal end of the tubular shaft 84 and distal from the distal end of the insertion tube 30 when the basket assembly is deployed.

As described supra, control console 24 includes irrigation module 60 that delivers irrigation fluid to distal end 36. The multiple irrigation openings 98 can be angled to spray or otherwise disperse of the irrigation fluid to either a given electrode 40 or to tissue in heart 26. Since electrodes 40 do not include irrigation openings that deliver irrigation fluid, the configuration described hereinabove enables heat to be transferred from the tissue (i.e., during an ablation procedure) to the portion of the electrodes on the inner side of the spines 214, and the electrodes 40 can be cooled by aiming the irrigation fluid, via irrigation openings 98, at the portion of the electrodes 40 on the inner side of the spines 214. Spine retention hub electrode (usable as a reference electrode) 99 disposed at a distal end of retention hub 90 can be used in combination with electrodes 40 on the spines 214, or alternatively, can be used independently from electrodes 40 for reference mapping or ablation.

FIGS. 4A and 4B are schematic pictorial illustrations showing a profile outline of a basket assembly 38A, 38B such that when the basket assembly is deployed the spines define a three-dimensional shape including the profile. The basket assembly can be approximately spheroid including an approximately circular profile as shown in FIG. 4A. The basket assembly can have an approximately oblate-spheroid shape including an approximately elliptical profile as shown in FIG. 4B. Although not every variation of shape is shown or described herein, one skilled in the art will appreciate that spines 214 can be further configured to form other various shapes as would be suitable for the particular application.

By including spines 214 configured to form various shapes when in the expanded form, basket assembly 38 can be configured to position the various electrodes 40 attached to spines 214 at various locations, with each location being nearer or farther from the distal end of tubular shaft 84. For example, electrode 40 attached to spine 214 illustrated in FIG. 3A near the middle of spine 214 would be farther from the distal end of tubular shaft 84 than spine 214 illustrated in FIG. 3B when basket assembly 38 is in the expanded form. In addition, each spine 214 may have an elliptical (e.g., circular) or rectangular (that may appear to be flat) cross-section, and include a flexible, resilient material (e.g., a shape-memory alloy such as nickel-titanium (also known as Nitinol), cobalt chromium, or any other suitable material).

FIGS. 5, 6A and 6B are schematic pictorial illustrations showing views of spines 214 forming basket assembly 38. FIG. 5 provides one example of how planar sheet of material 210 as a base material may be assembled together with tubular shaft 84 whereby each spine 214 bends or curves when respective attachment ends 217 are connected to spine retention hub 90. As shown in FIG. 6A, the spines 214 can be formed from a single sheet of planar material 910 along with an additional second layer to form a generally star shape. In other words, spines 214 can be formed from the single sheet of planar material such that the spines 214 converge toward a central spine intersection 211. The intersection 211 can be a solid piece of material (as shown in FIG. 6A) or include one or more cutouts 212 (as shown in FIG. 6B). Basket assembly 38 can include a number of spines 214 ranging from about four to about ten spines from a single sheet of planar material 210 as base layer.

FIGS. 7 and 8A-8D are schematic pictorial illustrations of cutting patterns for various linear spines patterns 802 from a planar sheet of material 210. As described supra, planar sheet of material 210 can include a number of spines 214 ranging from about four to about ten spines. As illustrated in FIG. 7, planar sheet of material 210 can include central intersection 811 and spine pattern 802, which includes one or both of longitudinal scores 817 and transverse scores 818. In any of the embodiments disclosed herein, planar sheet of material 810 can also include a central intersection 811 and spine patterns 802 including an equiangular pattern 813. Planar sheet of material 810 can include spine patterns including a number of spine patterns 802 forming spines 814 in basket assembly 38. As would be understood by one of skill in the art, adjusting the number of spine patterns 802 may impact a number of factors including, without limitation, stability, flexibility, surface contact, and ablation capacity of medical probe 22.

FIG. 8A through 8D provide example spine patterns 802A, 802B, 802C, 802D, although additional spine patterns are contemplated. Similar to the above planar sheet of material 210, spine patterns 802A-802D can include a respective central intersection 811 and a respective equiangular pattern 813A-813D. As would be appreciated by one of skill in the art, as the number of spines added to spine pattern 802A-802D, the angle for equiangular pattern 813A-813D may change. In each of these examples provided, planar sheet of material 210A, 210B, 210C, 210D may also include central intersections and spine patterns including equiangular patterns. Although not depicted in FIGS. 8A-8D, planar sheet of material 210A-210D can include one or both of longitudinal scores 817 and transverse scores 818.

FIG. 9 is a schematic pictorial illustration of a cutting pattern for various linear spine patterns including one or more cutouts at a central spine intersection from a planar sheet of material. As described supra, planar sheet of material 210E may include a spine pattern 802C including one cutout 912A at central intersection 911. Planar sheet of material 210E can include one or both of longitudinal scores 817 and transverse scores 818 as shown in FIG. 7.

FIG. 10 is a flowchart illustrating a method 1000 of manufacturing a basket assembly 38, in accordance with an embodiment of the present invention. Method 1000 can include cutting 1002 a planar sheet of a second material 210 to form a second layer (base layer) 218 for a plurality of linear spines 214 having a central spine intersection 211. Cutting 1002 the plurality of linear spines 214 can include cutting from a pattern (e.g., one or pattern 802A-802D) including longitudinal and transverse scores 817, 818. The planar sheet of resilient material can include shape-memory alloy such as nickel-titanium (also known as Nitinol), cobalt chromium, or any other suitable material. Method 1000 can include cutting 1004 a center hole at the central spine intersection 211 of the second layer 218. In some examples, steps 1002 and 1004 may occur as simultaneous steps or as a sequence of steps. As an alternative to steps 1002 and 1004, metallic strands can be shaped similar to the pattern formed by cutting the planar sheet in steps 1002 and 1004. Overmolding 1006 a second material (e.g., PEEK) on the second layer 218 to form a first layer 216 for the plurality of linear spines 214.

Cutting 1008 an aperture 124 in the first layer at the central spine intersection 211. Inserting 1008 a central electrode 120A, 120B into the aperture 124 of the first layer.

Method 1000 can optionally include attaching a first extrusion layer 220 to partially cover end portions of each spine 214, attaching a second extrusion layer 222 to cover each spine 214 and the first extrusion layer 220 covering each spine 214, inserting one or more ring electrodes 40 around each spine 214, and fitting ends of the plurality of spines 214 to a tubular shaft sized to traverse vasculature such that the central spine intersection 211 is positioned at a distal end of the medical probe 22 and respective spines 214 are movable from a tubular configuration to a bowed configuration. Method 1000 may also include cutting radial cutouts (e.g. 912A) in the first material in each of the plurality of spines 214 proximate the central spine intersection 211.

As will be appreciated by one skilled in the art, method 1000 can include any of the various features of the disclosed technology described herein and can be varied depending on the particular configuration. Thus, method 1000 should not be construed as limited to the particular steps and order of steps explicitly described herein. It is noted that while the preference for the exemplary embodiments of the medical probe is for IRE or PFA, it is within the scope of the present invention to also use the medical probe separately only for RF ablation (unipolar mode with an external grounding electrode or bipolar mode) or in combination with IRE and RF ablations sequentially (certain electrodes in IRE mode and other electrodes in RF mode) or simultaneously (groups of electrodes in IRE mode and other electrodes in RF mode).

The embodiments described above are examples, and the present invention is not limited by what has been particularly shown and described hereinabove. Rather, the scope of the invention includes both combinations and sub combinations of the various features described and illustrated hereinabove, as well as variations and modifications thereof which would occur to persons skilled in the art upon reading the foregoing description and which are not disclosed in the prior art.

In some examples, disclosed devices (e.g., spines, basket assemblies, electrodes, and/or medical probes) and methods may involve one or more of the following clauses:

Clause 1: An expandable basket assembly for a medical probe, comprising: a single unitary structure comprising a plurality of spines converging at a central spine intersection, the central spine intersection being positioned on a longitudinal axis of the expandable basket assembly at a distal end thereof; the plurality of spines comprise: a first layer; a second layer attached to the first layer and comprising a central cutout about the central spine intersection that exposes the first layer at the central spine intersection; and a central electrode attached to the first layer at the central spine intersection via a central aperture in the first layer at the central spine intersection, wherein the second layer is configured to articulate independently of the first layer at the central spine intersection.

Clause 2: The expandable basket assembly of clause 1, wherein the first layer comprises polyether ether ketone (PEEK), liquid crystal polymer (LCP), or both.

Clause 3: The expandable basket assembly of clauses 1 or 2, wherein the second layer comprises nitinol, cobalt chromium, or both.

Clause 4: The expandable basket assembly according to any one of clauses 1 to 3, wherein the plurality of spines comprises four to ten spines of the plurality of spines.

Clause 5: The expandable basket assembly according to clause 4, wherein the plurality of spines comprises six spines.

Clause 6: The expandable basket assembly according to any one of clauses 1 to 5, wherein the plurality of spines form an approximately spherical shape.

Clause 7: The expandable basket assembly according to any one of clauses 1 to 5, wherein the plurality of spines form an approximately oblate-spheroid shape.

Clause 8: The expandable basket assembly according to any one of clauses 1 to 7, further comprising one or more electrodes coupled to each of the spines, each electrode defining a lumen through the electrode so that a spine extends through the lumen of each of the one or more electrodes.

Clause 9: The expandable basket assembly according to clause 8, wherein each electrode comprises a wire relief adjacent the lumen to allow for one or more wires to extend adjacent to the lumen.

Clause 10: The expandable basket assembly according to clause 8 or 9, wherein the lumen is disposed symmetrically about a longitudinal axis of the electrode.

Clause 11: The expandable basket assembly according to any one of clauses 8 to 10, wherein the one or more electrodes are configured to deliver electrical pulses for irreversible electroporation, the pulses having a peak voltage of at least 900 volts (V).

Clause 12: The expandable basket assembly according to any one of clauses 8 to 11, wherein the central electrode is electrically isolated from the one or more electrodes coupled to each of the spines.

Clause 13: The expandable basket assembly according to any one of clauses 12, wherein the central electrode is spaced apart from the second layer.

Clause 14: The expandable basket assembly according to any one of clauses 1 to 13, wherein the central electrode comprises a disc- or button-shape.

Clause 15: The expandable basket assembly according to any one of clauses 1 to 14, wherein the second layer comprises a plurality of radial cutouts extending from the central cutout along the second layer of each spine.

Clause 16: The expandable basket assembly according to any of clauses 1 to 15, wherein the first layer is an inner layer and the second layer is an outer layer.

Clause 17: The expandable basket assembly according to any of clauses 1 to 15, wherein the first layer is an outer layer and the first layer is an outer layer.

Clause 18 An expandable basket assembly for a medical probe, comprising: a single unitary structure comprising a plurality of spines converging at a central spine intersection, the central spine intersection being positioned on a longitudinal axis of the expandable basket assembly at a distal end thereof; and the plurality of spines comprise: an outer layer; an inner layer attached to the outer layer; one or more extrusion layers at least partially covering each spine; a central electrode attached to the outer layer at the central spine intersection via a central aperture in the outer layer at the central spine intersection; and one or more electrodes attached to each spine and disposed over a portion of the one or more extrusion layers.

Clause 19: A method of constructing a medical probe, the method comprising: cutting a planar sheet of a second material to form a second layer of a plurality of spines having a central spine intersection; cutting a center hole at the central spine intersection; overmolding a first material on the second layer for form a first layer; cutting aperture in the first layer at the central spine intersection; and inserting a central electrode into the aperture.

Clause 20: The method of according to clause 19, further comprising: attaching a first extrusion layer to partially cover end portions of each spine; attaching a second extrusion layer to cover each spine and the first extrusion layer covering each spine; inserting one or more ring electrodes around each spine; and fitting ends of the plurality of spines to a tubular shaft sized to traverse vasculature such that the central spine intersection is positioned at a distal end of the medical probe and respective spines are movable from a tubular configuration to a bowed configuration.

Clause 21: The method of according to clause 19, further comprising: cutting radial cutouts in the first material in each of the plurality of spines proximate the central spine intersection.

What is claimed is:

1. An expandable basket assembly for a medical probe, comprising:

a single unitary structure comprising a plurality of spines converging at a central spine intersection, the central spine intersection being positioned on a longitudinal axis of the expandable basket assembly at a distal end thereof;

the plurality of spines comprise:

a first layer;

a second layer attached to the first layer and comprising a central cutout about the central spine intersection that exposes the first layer at the central spine intersection, the second layer comprising a plurality of radial cutouts extending from the central cutout along the second layer of each spine; and a central electrode attached to the first layer at the central spine intersection via a central aperture in the first layer at the central spine intersection.

2. The expandable basket assembly of claim 1, wherein the first layer comprises polyether ether ketone (PEEK), liquid crystal polymer (LCP), or both.

3. The expandable basket assembly according to claim 2, wherein the second layer comprises nitinol, cobalt chromium, or both.

4. The expandable basket assembly according to claim 1, wherein the plurality of spines comprises four to ten spines of the plurality of spines.

5. The expandable basket assembly according to claim 4, wherein the plurality of spines comprises six spines.

6. The expandable basket assembly according to claim 1, further comprising one or more electrodes coupled to each of the spines, each electrode defining a lumen through the electrode so that a spine extends through the lumen of each of the one or more electrodes.

7. The expandable basket assembly according to claim 6, wherein each electrode comprises a wire relief adjacent the lumen to allow for one or more wires to extend adjacent to the lumen.

8. The expandable basket assembly according to claim 6, wherein the lumen is disposed symmetrically about a longitudinal axis of each of the one or more electrodes.

9. The expandable basket assembly according to claim 6, wherein the one or more electrodes are configured to deliver electrical pulses for irreversible electroporation, the pulses having a peak voltage of at least 900 volts (V).

10. The expandable basket assembly according to claim 6, wherein the central electrode is electrically isolated from the one or more electrodes coupled to each of the spines.

11. The expandable basket assembly according to claim 1, wherein the plurality of spines form an approximately spherical shape.

12. The expandable basket assembly according to claim 1, wherein the plurality of spines form an approximately oblate-spheroid shape.

13. The expandable basket assembly according to claim 1, wherein the central electrode is spaced apart from the second layer.

14. The expandable basket assembly according to claim 1, wherein the central electrode comprises a disc- or button-shape.

15. The expandable basket assembly according to claim 1, wherein the first layer is an inner layer and the second layer is an outer layer.

16. The expandable basket assembly according to claim 1, wherein the first layer is an outer layer and the first layer is an outer layer.

17. The expandable basket assembly of claim 1,
the first layer comprising polyether ether ketone (PEEK), liquid crystal polymer (LCP), or both,
the second layer comprising nitinol, cobalt chromium, or both,
the plurality of spines comprising six spines,
the plurality of spines forming an approximately oblate-spheroid shape,
further comprising one or more electrodes coupled to each of the spines, each electrode defining a lumen through the electrode so that a spine extends through the lumen of each of the one or more electrodes, the lumen being disposed symmetrically about a longitudinal axis of each of the one or more electrodes, the one or more electrodes being configured to deliver electrical pulses for irreversible electroporation, the pulses having a peak voltage of at least 900 volts (V), the central electrode being electrically isolated from the one or more electrodes coupled to each of the spines,
the central electrode being spaced apart from the second layer, and
the central electrode comprising a disc- or button-shape.

18. An expandable basket assembly for a medical probe, comprising:
a single unitary structure comprising a plurality of spines converging at a central spine intersection, the central spine intersection being positioned on a longitudinal axis of the expandable basket assembly at a distal end thereof; and
the plurality of spines comprise:
an outer layer comprising a central cutout and a plurality of radial cutouts extending from the central cutout along the outer layer of each spine;
an inner layer attached to the outer layer, the central cutout exposing the inner layer at the central spine intersection;
one or more extrusion layers at least partially covering each spine;
a central electrode attached to the inner layer at the central spine intersection via a central aperture in the inner layer at the central spine intersection; and
one or more electrodes attached to each spine and disposed over a portion of the one or more extrusion layers.

19. A method of constructing a medical probe, the method comprising:
cutting a planar sheet of a second material to form a second layer of a plurality of spines having a central spine intersection;
cutting a center cutout at the central spine intersection;
cutting radial cutouts that extend from the center cutout along the second layer of each spine;
overmolding a first material on the second layer for forming a first layer;
cutting aperture in the first layer at the central spine intersection; and
inserting a central electrode into the aperture.

20. The method of according to claim 19, further comprising:
attaching a first extrusion layer to partially cover end portions of each spine;
attaching a second extrusion layer to cover each spine and the first extrusion layer covering each spine;
inserting one or more ring electrodes around each spine; and
fitting ends of the plurality of spines to a tubular shaft sized to traverse vasculature such that the central spine intersection is positioned at a distal end of the medical probe and respective spines are movable from a tubular configuration to a bowed configuration.

* * * * *